United States Patent [19]
Watanabe et al.

[11] Patent Number: 6,015,552
[45] Date of Patent: Jan. 18, 2000

[54] USE OF NERVE GROWTH FACTOR-2 (NGF-2) /NEUROTROPHIN-3 (NT-3) TO PROMOTE LEUKOCYTE PROLIFERATION

[75] Inventors: Tatsuya Watanabe; Sumie Yoshitomi, both of Osaka; Reiko Sasada, Nagaokakyo, all of Japan

[73] Assignee: Takeda Chemical Industries, Ltd., Osaka, Japan

[21] Appl. No.: 08/910,691

[22] Filed: Aug. 13, 1997

Related U.S. Application Data

[62] Division of application No. 08/074,969, Jun. 4, 1993, abandoned.

[30] Foreign Application Priority Data

Jun. 8, 1992 [JP] Japan ................................. 4-147749

[51] Int. Cl.$^7$ ........................... A61K 38/19; A61K 38/18
[52] U.S. Cl. ............................... 424/85.1; 514/2
[58] Field of Search ................. 514/2; 424/85.1

[56] References Cited

U.S. PATENT DOCUMENTS

| | | |
|---|---|---|
| 5,169,764 | 12/1992 | Shooter et al. . |
| 5,229,500 | 7/1993 | Barde et al. . |
| 5,235,043 | 8/1993 | Collins et al. . |
| 5,288,487 | 2/1994 | Kawashima et al. . |
| 5,488,099 | 1/1996 | Persson et al. . |
| 5,606,031 | 2/1997 | Lile et al. . |

FOREIGN PATENT DOCUMENTS

| | | |
|---|---|---|
| 0 370 171 | 5/1990 | European Pat. Off. . |
| 0 386 752 | 9/1990 | European Pat. Off. . |
| 0 444 638 A2 | 9/1991 | European Pat. Off. . |
| WO 9103569 | 3/1991 | WIPO . |

OTHER PUBLICATIONS

Hannestad, J., et al. (1995) *J. Neuroimmunol.* 58: 131–37.
Shinoda, M., et al. (1996) *Brain Res.* 722: 153–67.
Iwane, M., et al. (1994) *Appl. Microbiol. Biotechnol.* 41: 225–32.
Y. Kaisho et al.; Febs Letters, vol. 266, No. 1,2 (1990) pp. 187–191.
H. Matsuda, et al., Proc. Natl. Acad. Sci. USA vol. 85, pp. 6508–6512 (1988).
P. Maisonpierre, et al., Science, vol. 247 pp. 1446–1451 (1990).
P. Maisonpierre, et al., Genomics, vol. 10, No. 3, pp. 558–568 (1991).
Ernfors, et al., Proc. Nat'l Acad. Sci. vol. 87, No. 14, pp. 5454–5458 (1990).
Jones, et al., Proc. Nat'l Acad. Scie. vol. 87, No. 20, pp. 8060–8064 (1990).
Hohn, et al., Nature, Vo. 344, Issue No. 6264, pp. 449–441 (1990).

*Primary Examiner*—David L. Fitzgerald
*Attorney, Agent, or Firm*—Dike, Bronstein, Roberts & Cushman, LLP; David G. Conlin; George W. Neuner

[57] ABSTRACT

Human Nerve Growth Factor-2 (NGF-2, also known as Neurotrophin-3 or NT-3) has been found to promote the proliferation of peripheral blood leukocytes. The invention provides methods using hNGF-2 polypeptides in the treatment of neutropenia.

12 Claims, 16 Drawing Sheets

```
                                                                                        58
GAATTCGGCC ATG TCC ATC TTG TTT TAT GTG ATA TTT CTC GCT TAT CTC CGT GGC ATC
           Met Ser Ile Leu Phe Tyr Val Ile Phe Leu Ala Tyr Leu Arg Gly Ile

118
CAA GGT AAC AAC ATG GAT CAA AGG AGT TTG CCA GAA GAC TCG CTC AAT TCC CTC ATT ATT
Gln Gly Asn Asn Met Asp Gln Arg Ser Leu Pro Glu Asp Ser Leu Asn Ser Leu Ile Ile

178
AAG CTG ATC CAG GCA GAT ATT TTG AAA AAC AAG CTC TCC AAG CAG ATG GTG GAC GTT AAG
Lys Leu Ile Gln Ala Asp Ile Leu Lys Asn Lys Leu Ser Lys Gln Met Val Asp Val Lys

238
GAA AAT TAC CAG AGC ACC CTG CCC AAA GCT GAG GCT CCC CGA GAG CCG GAG CGG GGA GGG
Glu Asn Tyr Gln Ser Thr Leu Pro Lys Ala Glu Ala Pro Arg Glu Pro Glu Arg Gly Gly

298
CCC GCC AAG TCA GCA TTC CAG CCA GTG ATT GCA ATG GAC ACC GAA CTG CTG CGA CAA CAG
Pro Ala Lys Ser Ala Phe Gln Pro Val Ile Ala Met Asp Thr Glu Leu Leu Arg Gln Gln

358
AGA CGC TAC AAC TCA CCG CGG GTC CTG AGC GAC AGC ACC CCC TTG GAG CCC CCG CCC
Arg Arg Tyr Asn Ser Pro Arg Val Leu Ser Asp Ser Thr Pro Leu Glu Pro Pro Pro

418
TTG TAT CTC ATG GAG GAT TAC GTG GGC AGC CCC GTG GTG GCG AAC AGA ACA TCA CGG CGG
Leu Tyr Leu Met Glu Asp Tyr Val Gly Ser Pro Val Val Ala Asn Arg Thr Ser Arg Arg

478
AAA CGG TAC GCG GAG CAT AAG AGT CAC CGA GGG GAG TAC TCG GTA TGT GAC AGT GAG AGT
Lys Arg Tyr Ala Glu His Lys Ser His Arg Gly Glu Tyr Ser Val Cys Asp Ser Glu Ser
```

FIG. 7A

```
CTG TGG GTG ACC GAC AAG TCA TCG GCC ATC GAC ATT CGG GGA CAC CAG GTC ACG GTG CTG      538
Leu Trp Val Thr Asp Lys Ser Ser Ala Ile Asp Ile Arg Gly His Gln Val Thr Val Leu

GGG GAG ATC AAA ACG GGC AAC TCT CCC GTC AAA CAA TAT TTT TAT GAA ACG CGA TGT AAG      598
Gly Glu Ile Lys Thr Gly Asn Ser Pro Val Lys Gln Tyr Phe Tyr Glu Thr Arg Cys Lys

GAA GCC AGG CCG GTC AAA AAC GGT TGC AGG GGT ATT GAT GAT AAA CAC TGG AAC TCT CAG      658
Glu Ala Arg Pro Val Lys Asn Gly Cys Arg Gly Ile Asp Asp Lys His Trp Asn Ser Gln

TGC AAA ACA TCC CAA ACC TAC GTC CGA GCA CTG ACT TCA GAG AAC AAT AAA CTC GTG GGC      712
Cys Lys Thr Ser Gln Thr Tyr Val Arg Ala Leu Thr Ser Glu Asn Asn Lys Leu Val Gly

TGG CGG TGG ATA CGG ATA GAC ACG TCC TGT GTG TGT GCC TTG TCG AGA AAA ATC GGA AGA      778
Trp Arg Trp Ile Arg Ile Asp Thr Ser Cys Val Cys Ala Leu Ser Arg Lys Ile Gly Arg

ACA TGA ATT GGC ATC TCT CCC CAT ATA TAA ATT ATT ACT TTA AAT TAT ATG ATA TGC ATG      838
Thr

TAG CAT ATA AAT GTT TAT ATT GTT TTT ATA TAT ATT GTT TTT ATA TAT AAG TTG ACC TTT ATT TAT TAA ACT      898

TCA GCA ACC CTA CAG TAT ATA GGC TTT TTT CTC AAT AAA ATC AGT GTG CTT GCC TTC CCT      958

CAG GCA GAT CT                                                                        969
```

FIG. 7B

```
TAG CTT GCC GCC ACC ATG TCC ATG TTG TTC TAC ACT CTG ATC ACA GCT TTT CTG ATC GGC      60
            Met Ser Met Leu Phe Tyr Thr Leu Ile Thr Ala Phe Leu Ile Gly

ATA CAG GCG GAA CCA CAC TCA GAG AGC AAT GTC CCT GCA GGA CAC ACC ATC CCC CAA GTC     120
Ile Gln Ala Glu Pro His Ser Glu Ser Asn Val Pro Ala Gly His Thr Ile Pro Gln Val

CAC TGG ACT AAA CTT CAG CAT TCC CTT GAC ACT GCC CGC AGA GCC CGC AGC GCC CCG         180
His Trp Thr Lys Leu Gln His Ser Leu Asp Thr Ala Arg Arg Ala Arg Ser Ala Pro

GCA GCG GCG ATA GCT GCA CGC GTG GCG GGG CAG ACC CGC AAC ATT ACT GTG GAC CCC AGG     240
Ala Ala Ala Ile Ala Ala Arg Val Ala Gly Gln Thr Arg Asn Ile Thr Val Asp Pro Arg

CTG TTT AAA AAG CGG CGA CTC CGT TCA CCC CGT GTG CTG TTT AGC ACC CAG CCT CCC CGT     300
Leu Phe Lys Lys Arg Arg Leu Arg Ser Pro Arg Val Leu Phe Ser Thr Gln Pro Pro Arg

GAA GCT GCA GAC ACT CAG GAT CTG GAC TTC GAG GTC GGT GCT GCC GCC CCC TTC AAC AGG     360
Glu Ala Ala Asp Thr Gln Asp Leu Asp Phe Glu Val Gly Ala Ala Ala Pro Phe Asn Arg

ACT CAC AGG AGC AAG CGC TAC GCG GAG CAT AAG AGT CAC CGA GGG GAG TAC TCG GTA TGT     420
Thr His Arg Ser Lys Arg Tyr Ala Glu His Lys Ser His Arg Gly Glu Tyr Ser Val Cys

GAC AGT GAG AGT CTG TGG GTG ACC GAC AAG TCA TCG GCC ATC GAC ATT CGG GGA CAC CAG     480
Asp Ser Glu Ser Leu Trp Val Thr Asp Lys Ser Ser Ala Ile Asp Ile Arg Gly His Gln
```

FIG. 8A

```
GTC ACG GTG CTG GGG GAG ATC AAA ACG GGC AAC TCT CCC GTC AAA CAA TAT TTT TAT GAA    540
Val Thr Val Leu Gly Glu Ile Lys Thr Gly Asn Ser Pro Val Lys Gln Tyr Phe Tyr Glu

ACG CGA TGT AAG GAA GCC AGG CCG GTC AAA AAC GGT TGC AGG GGT ATT GAT GAT AAA CAC    600
Thr Arg Cys Lys Glu Ala Arg Pro Val Lys Asn Gly Cys Arg Gly Ile Asp Asp Lys His

TGG AAC TCT CAG TGC AAA ACA TCC CAA ACC TAC GTC CGA GCA CTG ACT TCA GAG AAC AAT    660
Trp Asn Ser Gln Cys Lys Thr Ser Gln Thr Tyr Val Arg Ala Leu Thr Ser Glu Asn Asn

AAA CTC GTG GGC TGG CGG ATA CGG TGG ATA GAC ACG TCC TGT GTG TGT GCC TTG TCG AGA    720
Lys Leu Val Gly Trp Arg Ile Arg Trp Ile Asp Thr Ser Cys Val Cys Ala Leu Ser Arg

AAA ATC GGA AGA ACA TGA ATT GGC ATC TCT CCC CAT ATA TAA ATT ATT ACT TTA AAT TAT    780
Lys Ile Gly Arg Thr

ATG ATA TGC ATG TAG CAT ATA AAT GTT TAT ATT GTT TTT ATA TAT TAT AAG TTG ACC TTT    840

ATT TAT TAA ACT TCA GCA ACC CTA CAG TAT ATA GGC TTT TTT CTC AAT AAA ATC AGT GTG    900

CTT GCC TTC CCT CAG GCA GAT CT                                                      923
```

FIG. 8B

Tyr Ala Glu His Lys Ser His Arg Gly Glu Tyr Ser Val Cys Asp Ser

Glu Ser Leu Trp Val Thr Asp Lys Ser Ser Ala Ile Asp Ile Arg Gly

His Gln Val Thr Val Leu Gly Glu Ile Lys Thr Gly Asn Ser Pro Val

Lys Gln Tyr Phe Tyr Glu Thr Arg Cys Lys Glu Ala Arg Pro Val Lys

Asn Gly Cys Arg Gly Ile Asp Asp Lys His Trp Asn Ser Gln Cys Lys

Thr Ser Gln Thr Tyr Val Arg Ala Leu Thr Ser Glu Asn Asn Lys Leu

Val Gly Trp Arg Trp Ile Arg Ile Asp Thr Ser Cys Val Cys Ala Leu

Ser Arg Lys Ile Gly X

FIG. 22

USE OF NERVE GROWTH FACTOR-2 (NGF-2) /NEUROTROPHIN-3 (NT-3) TO PROMOTE LEUKOCYTE PROLIFERATION

This is a divisional of application Ser. No. 08/074,969 filed on Jun. 4, 1993, now abandoned.

FIELD OF THE INVENTION

The present invention relates to a therapeutic agent for neutropenia containing human nerve growth factor-2.

BACKGROUND OF THE INVENTION

As to neurotrophic factors, a number of factors have been discovered, since nerve growth factor (NGF) was discovered by Levi-Monntalcini, *Anu. N. Y. Acad. Sci.*, 55, 330 (1952) and Cohen et al., *Proc. Natl. Acad. Sci. USA,* 40, 1014 (1954). These factors have been considered to bring a variety of functions such as differentiation, maturation, survival, maintenance of functions and proliferation. These factors include brain-derived neurotrophic factor (BDNF) [Y. A. Barde et al., *EMBO J.,* 1, 549–553 (1982)] and ciliary neurotrophic factor (CNTF) [D. Watters et al., *J. Neurochem.,* 49, 705–713 (1987)] as well as NGF mentioned above.

Human nerve growth factor 2 (NGF-2) is disclosed as polypeptide (I) in European Patent Publication No. 386,752, and published in *FEBS Letters,* 266, 187–191 (1990). The same factor is reported as NT-3 in documents such as Hohn et al., Nature, 344, 399 (1990), and disclosed in PCT International Publication No. W091/03569.

In this specification, human nerve growth factor-2 is sometimes also briefly referred to as human NGF-2/NT-3. With respect to human NGF-2/NT-3, (1) human NGF-2/NT-3 gene is strongly expressed in the kidney and in the hippocampus and the cerebellum in the brain, (2) the gene is expressed more strongly in the neonates than in the mature animals, and (3) the gene acts on nerve cells such as nodose ganglion-derived nerve cells on which NGF or BDNF does not act or weakly acts. From these facts, it is conceivable that NGF-2/NT-3 importantly acts upon development of nerve systems.

In differentiation of the blood cells, pluripotent stem cells are first differentiated into lymphatic stem cells and myeloid stem cells. Next, the lymphatic stem cells are differentiated into T lymphocytes and plasma cells through several differentiation stages. The myeloid stem cells are differentiated into the basocytes, acidocytes, monocytes and macrophages, neutrophils, megakaryocytes and erythrocytes. It has been known that a number of hematopoietic factors such as colony stimulating factors and interleukins are concerned in the respective differentiation stages, and some of these factors are known to be clinically useful.

The hematopoietic factors such as various colony stimulating factors and interleukins are factors acting in the differentiation stages of the blood cells, and very few act on the blood cells in the final differentiation stage of the peripheral blood, for example, basocytes, acidocytes, monocytes and neutrophils, to allow their proliferation. NGF is known to stimulate colony formation in the peripheral blood [Proc. Natl. Acad. Sci., 85, 6508 (1988)].

SUMMARY OF THE INVENTION

The application of NGF-2/NT-3 to treatment of various central nervous system diseases has been attempted.

The present inventors discovered that NGF-2/NT-3 which is essentially different from NGF in the structure had the activity of stimulating the proliferation of the differentiated blood cells in the peripheral blood. Further, the present inventors discovered that the administration of this factor to animals caused the blood cells to significantly increase in number to exhibit complete response to treatment of neutropenia. Furthermore, this factor can be also useful for treatment of infection diseases and tumors.

The present invention provides an agent for treatment of neutropenia containing NGF-2/NT-3.

BRIEF DESCRIPTION OF THE DRAWINGS

FIGS. 7A–7B show a sequence of DNA coding for the pro region of NGF-2/NT-3 existing on plasmid pTB1339 obtained in Reference Example 4, DNA coding for NGF-2/NT-3 and DNA in the vicinity thereof;

FIGS. 8A–8B show a sequence of DNA coding for the pro region of NGF existing on plasmid pTB1344 obtained in Reference Example 6, DNA coding for NGF-2/NT-3 and DNA in the vicinity thereof;

FIG. 22 shows an amino acid sequence of human NGF-2; and

DESCRIPTION OF THE PREFERRED EMBODIMENTS

Figure 1:
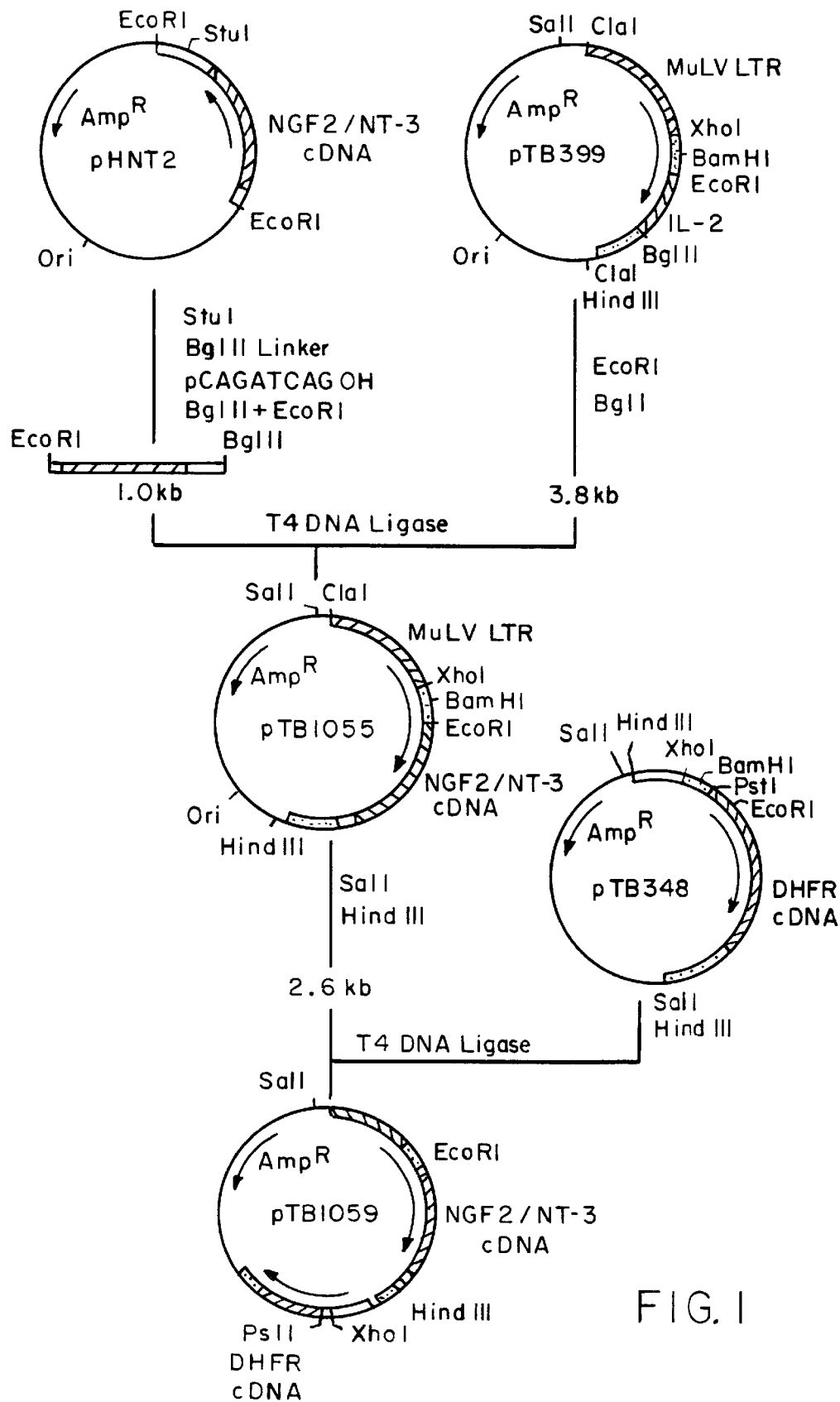
FIG. 1 is a schematic representation showing the construction of plasmid pTB1059 obtained in Reference Example 4.

In the present invention NGF-2/NT-3 may be any substances, as long as they have neurotrophic factor activity, namely functions such as differentiation, survival and maintenance of functions of nerve cells. Examples thereof include natural NGF-2/NT-3 produced in animal bodies or animal cells, NGF-2/NT-3 produced by recombinant technology, and related substances thereof. These substances may have sugar chains at their peptide chains or not.

Specifically, they include polypeptide (I) (human NGF-2/NT-3) (European Patent Publication No. 386,752 and Japanese Patent Unexamined Publication No. 3-204897) having an amino acid sequence represented by the sequence shown in FIG. 22 (SEQ ID NO:12, in FIG. 22, X is Arg or Arg Thr) and fragments consisting of a partial amino acid sequence necessary for biological or immunological activity thereof. Examples of the above-mentioned fragments include a fragment lacking 5 amino acid residues from the amino terminus of polypeptide (I) (European Patent Publication No. 499,993) and a fragment lacking several amino acid residues from the carboxyl terminus. Further, a mutein of polypeptide (I) having the amino acid sequence shown in FIG. 22 may be also used in the present invention.

Such NGF-2/NT-3 are obtained essentially by variations of the amino acid sequences of the original peptides or proteins. Such variations include addition of amino acid(s), deletion of constituent amino acid(s) and substitution of constituent amino acid(s) by different amino acid(s). Further, NGF-2/NT-3 muteins introduced by glycosylation site are included in such variations.

Such addition of amino acid(s) includes addition of at least one amino acid, including methionine derived from the initiation codon used for peptide expression and a signal peptide, as long as NGF-2/NT-3 characteristics are not lost. More preferable amino acids include some or all of the amino acid sequences of proteins which have homology with the NGF or BDNF and which exhibit activities similar to those of the NGF-2/NT-3.

Such deletion of constituent amino acid(s) includes deletion of at least one NGF-2/NT-3 constituent amino acid, excluding cysteine, as long as NGF-2/NT-3 characteristics are not lost. There may be mentioned the mutein which lacks 1 to 7 amino acid residues, preferably 1 to 5 amino acid residues from the amino terminus of polypeptide (I) and the mutein which lacks one or more amino acid residues from the regions of the 41st to the 48th, the 57th to the 61st and the 91st to the 94th amino acid residues of the polypeptide (I).

Such substitution of constituent amino acid(s) by different amino acid(s) includes substitution of at least one NGF-2/NT-3 constituent amino acid, excluding cysteine, by at least one different amino acid, as long as NGF-2/NT-3 characteristics are not lost. There may be mentioned, as such constituent amino acids, isoleucine, lysine, threonine, alanine, serine, proline, valine, glutamic acid, arginine, glycine and asparagine, preferably at the position in the regions of the 41st to 48th, the 57th to 61st and the 91st to 94th amino acid residues as defined by the sequence shown in FIG. 22.

For example, when the constituent amino acid is isoleucine, the substituting amino acids include asparagine, threonine, valine, lysine, glycine, serine and proline. When the constituent amino acid is arginine, the substituting amino acids include glutamic acid, lysine and alanine. When the constituent amino acid is glycine, the substituting amino acids include threonine, isoleucine, lysine, glycine, serine, asparagine, proline and valine.

When the constituent amino acid is serine, the substituting amino acids include isoleucine, glutamic acid, threonine, glycine, asparagine, proline, valine and lysine. When the constituent amino acid is valine, the substituting amino acids include serine, isoleucine, proline, glycine, threonine, lysine and asparagine.

When the constituent amino acid is lysine, the substituting amino acids include isoleucine, threonine, glycine, asparagine, serine, proline, glutamic acid, alanine, arginine and valine.

When the constituent amino acid is threonine, the substituting amino acids include isoleucine, lysine, glycine, asparagine, serine, proline and valine.

When the constituent amino acid is asparagine, the substituting amino acids include isoleucine, threonine, glycine, lysine, serine, proline, glutamic acid and valine.

When the constituent amino acid is proline, the substituting amino acids include isoleucine, lysine, glycine, asparagine, serine, threonine and valine.

When the constituent amino acid is alanine, the substituting amino acids include glutamic acid, lysine and arginine.

When the constituent amino acid is glutamine acid, the substituting amino acids include alanine, lysine, serine, asparagine and arginine.

In the above substitution, the substitution of at least two constituent amino acids may be simultaneously carried out. In particular, it is preferable to substitute two or three constituent amino acids.

The muteins may be obtained by a combination of two or three of the above-mentioned addition, deletion and substitution.

In order to produce the muteins, site-directed mutagenesis is employed. This technique is well-known and described in R. F. Lather and J. P. Lecoq, *Genetic Engineering*, pp. 31–50, Academic Press (1983). Mutagenesis directed to oligonucleotide is described in M. Smith and S. Gillam, *Genetic Engineering: Principles and Methods*, Vol. 3, pp. 1–32, Plenum Press (1981).

NGF-2/NT-3 may also be chemically modified ones such as polyethylene glycol derivatives.

In the present invention, human NGF-2/NT-3 having the amino acid sequence shown in FIG. 22 is preferably used among others. Further, human NGF-2/NT-3 used in the present invention includes the amino acid sequence which has an additional methionine residue (Met) at the amino terminus of FIG. 22 and a mixture of the amino acid sequence having a methionine residue (Met) at the amino terminus and one having no methionine residue may be used.

The NGF-2/NT-3 in the present invention is low in toxicity, so that it can be safely used.

The NGF-2/NT-3 in the present invention increases the blood cells of the peripheral blood, for example, basocytes, acidocytes, monocytes and neutrophils, to accelerate functions thereof. The NGF-2/NT-3 in the present invention can therefore be used as therapeutic agents for neutropenia of animals, and further as therapeutic agents for infection diseases and tumors.

The animals include warm blooded mammals such as mice, cats, cattle, sheep, goats, pigs, rabbits and humans.

The therapeutic agents of the present invention are given to animals, thereby improving neutropenia and further symptoms accompanying infection diseases to promote the cures. When given to animals, the therapeutic agents of the present invention further also exhibit antitumor activity.

The agents are generally given parenterally. For example, the therapeutic agents of the present invention can be preferably given to animals by injection.

The amount of the therapeutic agents of the present invention used varies depending on the method for administration, the application purpose, etc. When given by injection, however, they are preferably given, for example, in a dosage of about 0.02 µg/kg to 0.02 mg/kg daily, based on the protein amount of NGF-2/NT-3.

When the therapeutic agents of the present invention are prepared in solution form, they are prepared by conventional pharmaceutically acceptable methods, using NGF-2/NT-3 in combination with solvents such as aqueous solvents (for example, distilled water), water-soluble solvents (for example, physiological saline and Ringer solution) and oily solvents (for example, sesame oil and olive oil). Additives may be added such as solubilizing adjuvants (for example, sodium salicylate and sodium acetate), buffers (for example, sodium citrate and glycerin), isotonic agents (for example, glucose and invert sugar), stabilizers (for example, human serum albumin and polyethylene glycol), preservatives (for example, benzyl alcohol and phenol) and soothing agents (for example, benzalkonium chloride and procaine hydrochloride) if necessary.

The pH of the solutions are adjusted to about 3 to 8, and preferably to about 5 to 7. Diluted acids (for example, diluted hydrochloric acid) or diluted alkalis (for example, diluted sodium hydroxide and diluted sodium hydrogencarbonate) are added to adjust the solutions to the above-mentioned pH range.

When the therapeutic agents of the present invention are prepared in solid form, solid preparations for intramuscular injection can be prepared by conventional pharmaceutically acceptable methods, for example, lyophilizing NGF-2/NT-3 or mixing solid (for example powdery) NGF-2/NT-3 with diluents (for example, distilled water, physiological saline and glucose), excipients (for example, carboxymethyl cellulose (CMC) and sodium alginate), preservatives (for example, benzyl alcohol, benzalkonium chloride and phenol) and soothing agents (for example, glucose solution, calcium gluconate and procaine hydrochloride).

In the preparation of the therapeutic agents of the present invention, the further incorporation of human serum albumin (HSA) in aqueous solvents containing NGF-2/NT-3 and the adjustment to pH 3 to 8 in the solution state advantageously result in a slight decrease in NGF-2/NT-3 activity during storage and in freezing or lyophilizing operations, and allow lyophilized products to show a clear appearance when they are dissolved again.

As HSA, any one may be used, but in order to apply this composition clinically, a quality for parenteral administration is desired. For example, using the sera of healthy volunteers as raw materials, HSA purified by fractionation according to the sixth method of ethanol fractionation of Cohen is used. HSA may contain sodium acetyltryptophan or sodium caprylate as a stabilizer.

When each component is dissolved to form an aqueous solution, the amount of HSA added to the aqueous solution is preferably about 0.1 to 50 mg per ml of aqueous solution, and more preferably about 0.5 to 20 mg per ml.

In the preparation of the therapeutic agents of the present invention, one or more of amino acids such as glycine, glutamic acid, aspartic acid, alanine and proline, particularly monoamino fatty amino acids or cyclic amino acids, monosaccharides such as glucose and mannose, sugar alcohols such as sorbit and mannitol, pharmaceutically acceptable salts and derivatives thereof may be added, in addition to the above-mentioned HSA.

When the additives are added to aqueous solutions of NGF-2/NT-3, the monosaccharides or the sugar alcohols are preferably added in an amount of about 10 to 100 mg per ml of aqueous solution, and the amino acids are preferably added in an amount of about 5 to 50 mg per ml.

In the above-mentioned preparation, when acidic amino acids such as glutamic acid are added to adjust the pH of the aqueous solutions to about 3 to 8, preferably about 5 to 7, the pH can be adjusted to a required value by adding the amino acids in the amounts specified above. Further, mineral acids such as hydrochloric acid and phosphoric acid or buffers such as succinic acid, tartaric acid and citric acid are used to adjust the pH to a required value, if necessary or when the above-mentioned acidic amino acids are not added.

The therapeutic agents of the present invention are preferably provided in the form of an aqueous solution, a frozen product or a lyophilized product, more preferably in the form of the lyophilized product among others.

The therapeutic agents of the present invention can be preferably prepared, for example, by the following method, to prevent the NGF-2/NT-3 active substances from attenuating.

HSA is added at the concentration specified above to aqueous solutions containing the NGF-2/NT-3 active substances if necessary, and the pH is adjusted by the above-mentioned method.

The monosaccharides, the sugar alcohols and the amino acids may also be added at the concentrations described above if necessary. Further, the isotonic agents and surface active agents may also be added if necessary. When substances other than HSA are added, the final pH of the solutions is adjusted to the above-mentioned pH by the method described above. The therapeutic agents of the present invention as the aqueous solutions thus obtained can also be used as raw materials for the following frozen and lyophilized products.

The therapeutic agents of the present invention as the frozen products can be prepared, for example, by freezing the above-mentioned aqueous solutions usually at a temperature of about −80 to −20° C. The frozen compositions are preferably stored at a temperature of −80 to −10° C.

The therapeutic agents of the present invention as the lyophilized products can be prepared, for example, by normally drying the above-mentioned frozen compositions under reduced pressure, or by subdividing the above-mentioned aqueous solutions or solutions obtained by melting the above-mentioned frozen compositions if necessary, freezing the solutions in the same manner as described above, and normally drying the frozen products under reduced pressure.

Further, the lyophilized products prepared by the above-mentioned method are dissolved again in dissolving solutions which contain, for example, the above-mentioned monosaccharides, sugar alcohols or amino acids, and the pH of which is adjusted with hydrochloric acid, etc. if necessary, whereby the therapeutic agents of the present invention in the solution state can be prepared.

When the lyophilized therapeutic agents of the present invention are prepared as preparations for injection, it is preferred that the aqueous solution of NGF-2/NT-3 and the additive-containing aqueous solution are each subjected to sterile filtration and mixed with each other, or that a mixed solution thereof is purified by sterile filtration before subdivision, subdivided into vials by aseptic manipulation, and then subjected to the above-mentioned lyophilization. In this case, the stability of the composition can be enhanced by evacuating spaces of the vials or replacing the air in the spaces with gaseous nitrogen.

When the lyophilized products are dissolved in the aqueous solution containing the amino acids, monosaccharides or sugar alcohols, the solutions are preferably used which are subjected to sterile filtration, subdivided into ampuls by aseptic manipulation, and then sterilized with steam.

In giving the therapeutic agents of the present invention, when the compositions are in solution form, they are used as the solutions for injection as such.

When the compositions are lyophilized and in solid form, they are dissolved in distilled water or physiological saline to use as solutions for injection. They can also be dissolved in dissolving solutions which contain monosaccharides, sugar alcohols or amino acids similar to those described above, and the pH of which is adjusted in a manner similar to that described above, if necessary.

The therapeutic agents comprising NGF-2/NT-3 of the present invention significantly increase the blood cells in the peripheral blood to accelerate the functions.

The therapeutic agents of the present invention are therefore effective for treatment of neutropenia, and further usable for treatment of infection diseases and tumors.

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

| | |
|---|---|
| DNA: | Deoxyribonucleic acid |
| A: | Adenine |
| C: | Cytosine |
| G: | Guanine |
| T: | Thymine |
| Ala: | Alanine |
| Arg: | Arginine |
| Asn: | Asparagine |
| Asp: | Aspartic acid |
| Cys: | Cysteine |
| Gln: | Glutamine |
| Glu: | Glutamic acid |
| Gly: | Glycine |
| His: | Histidine |
| Ile: | Isoleucine |
| Leu: | Leucine |
| Lys: | Lysine |
| Met: | Methionine |
| Phe: | Phenylalanine |
| Pro: | Proline |
| Ser: | Serine |
| Thr: | Threonine |
| Trp: | Tryptophan |
| Tyr: | Tyrosine |
| Val: | Valine |

Transformant CHO-N2-1 obtained in Reference Example 9 was deposited with the Institute for Fermentation, Osaka, Japan (IFO) under the accession number IFO 50307 on Jan. 22, 1991. This transformant was also deposited with the Fermentation Research Institute, the Agency of Industrial Science and Technology, the Ministry of International Trade and Industry (FRI) under the accession number FERM BP-3255 on January 29, 1991.

REFERENCE EXAMPLE 1

Construction of Human NGF Expression Vector (1)

*Escherichia coli* NM538 was infect ed with a λEMBL3 genomic library (Clontech) prepared from human leucocyte DNA, and about $3 \times 10^4$ clones thereof were spread on each soft agar plate. The plaques were transferred on nylon membranes (Hybond-N, Amersham), and then immersed in a 0.5 N NaOH-1.5M NaCl solution for 6 minutes to denature phage DNA, followed by immersion in a 0.5M Tris-HCl (pH 8.0)-1.5 M NaCl solution for 6 minutes. The membranes were immersed in a 2×SSC solution , and then air-dried, followed by treatment at 80° C. for 2 hours, to fix the DNA on the membranes.

On the other hand, a DNA fragment (0.38 kb) coding for human βNGF was chemically synthesized according to the known human NGF gene [A. Ullrich et al., *Nature,* 303, 821 (1983)], and labeled with $^{32}$P using a DNA labeling kit (Nippon Gene) to form a probe.

The filters on which the DNA was fixed were maintained at 65° C. for 16 hours in 10 ml of a solution of 6×SSC (1×SSC=0.15M NaCl, 0.015M sodium citrate), 5×Denhardt's, 0.5% SDS and 20 μg/ml denatured salmon sperm DNA, containing the labeled probe. After reaction, the filters were washed 3 times with a solution of 2×SSC and 0.1% SDS at room temperature for 5 minutes, and further twice with a solution of 1×SSC and 0.1% SDS at 60° C. for 60 minutes. After drying of the washed filters, radioautograms were taken, and the clones reactive to the probe were searched. Phage DNA was extracted from clone λβLN2113 obtained by this method, according to the method of Davis et al. [Davis et al., *Advanced Bacterial Genetics,* Cold Spring Harbor Laboratory (1980)].

Then, λβLN2113 was cleaved with SmaI and ApaI to cut out a DNA fragment (about 1 kb) containing a human NGF gene, and the DNA fragment was inserted into the SmaI and ApaI sites of plasmid pBluscript II SK$^+$ (Stratagene, U.S.A.) to obtain plasmid pNGFP107G.

The same DNA fragment was inserted into the SmaI and ApaI sites of plasmid pBluscript II SK$^-$ (Stratagene) to obtain pNGFM108G. The nucleotide sequence of the fragment inserted into pNGFP107G and pNGFM108G was determined by use of Sequenase (United States Biochemical Corporation). The determined nucleotide sequence completely was identified with the sequence described in *Nature,* 303, 821 (1983) in the protein coding region.

The above-mentioned phage λβ2113 DNA was cleaved with restriction enzyme BglII, and a DNA fragment (1.8 kb) containing human NGF is isolated. On the other hand, expression vector pKSV-10 for animal cells (Pharmacia) was cleaved with restriction enzyme BglII, and the resulting fragment was ligated to the above-mentioned DNA fragment (1.8 kb) containing the human NGF gene with T4 DNA ligase. Using the resulting solution, *E. coli* DH1 was transformed, and a plasmid was isolated from one of ampicillin-resistant transformants, *E. coli* DH1/pMNGF101. This plasmid was named pMNGF101.

REFERENCE EXAMPLE 2

Construction of Human NGF Expression Vector (2)

Plasmid pNGFP107G obtained in Reference Example 1 was cleaved with restriction enzymes BclI and ApaI, and a DNA fragment (0.8 kb) containing the human NGF gene was isolated. The resulting 0.8-kb BclI-ApaI fragment was mixed with chemical synthetic adaptors SN1, SN2 and SN3, and ligated thereto with T4 DNA ligase, followed by cleaving with BglII to obtain a 0.8-kb HindIII-BglII DNA fragment.

```
SN1: 5'-AGC TTG CCG CCA CCA TGT CCA TGT TGT TCT ACA  (SEQ ID NO:1)

CTC T-3'  (37mer)

SN2: 5'-GAT CAG AGT GTA GAA CAA CAT GGA CAT GGT GGC  (SEQ ID NO:2)

GGC A-3'  (37mer)

SN3: 5'-CAG ATC TGG GCC-3'  (12mer)               (SEQ ID NO:3)
         Bgl II Apa I
```

Plasmid pSV2-gpt [*Science*, 209, 1422 (1980)] was cleaved with restriction enzymes EcoRI and HindIII, and a 2.6-kb EcoRI-HindIII DNA fragment containing an SV40 promoter was isolated. Then, a 1.6-kb BglII-EcoRI fragment containing a poly A addition region was isolated from plasmid pMTVdhfr [*Nature*, 294, 228 (1981)].

The above-mentioned 2.6-kb EcoRI-HindIII DNA fragment containing the SV40 promoter, the 0.8-kb HindIII-BglII DNA fragment and the 1.6-kb Bgl II-EcoRI fragment

```
Primer 1: 5'TAC AGG TGA ATT CGG CCA TGT CCA TCT TG 3'   (SEQ ID NO:4)

Primer 2: 5'AGA GAT GCG AAT TCA TGT TCT TC 3'           (SEQ ID NO:5)
``` containing the poly A addition region were ligated to one another with T4 DNA ligase. Using this reaction solution, *E. coli* DH1 was transformed, and a plasmid was isolated from the ampicillin-resistant transformant (*E. coli* DH1/pMNGF201). This plasmid was named pMNGF201.

REFERENCE EXAMPLE 3

Construction of Human NGF Expression Vector (3)

Plasmid pMNGF201 obtained in Reference Example 2 was cleaved with HindIII, and the cleavage end was rendered flush by the DNA polymerase Klenow fragment reaction, followed by cleavage with BglII. Then, a DNA fragment of about 0.8 kb was isolated. On the other hand, plasmid pTB399 (described in Japanese Patent Unexamined Publication (Laid-open) No. 61-63282/86) was cleaved with EcoRI, and the cleavage end was rendered flush by the Klenow fragment reaction, followed by cleavage with BglII to obtain a DNA fragment of about 3.9 kb. Both of these fragments were linked and cyclized by T4 DNA ligase reaction to obtain plasmid pTB1054.

REFERENCE EXAMPLE 4

Construction of Human NGF-2/NT-3 Expression Vector (1) Plasmid pHNT2 containing human NGF-2/NT-3 (see European Patent Publication No. 386,752) was cleaved with restriction enzyme StuI, and a BglII linker was ligated thereto with T4 DNA ligase. The resulting DNA fragment was cleaved with restriction enzymes EcoRI and BglII, thereby obtaining a 1.0-kb DNA fragment containing human NGF-2/NT-3. On the other hand, expression plasmid pTB399 for animal cells [*Cell Struct. Funct.*, 12, 205 (1987)] was cleaved with restriction enzymes EcoRI and BglII to obtain a DNA fragment of about 3.8 kb. Both the DNA fragments were ligated to each other with T4 DNA ligase to obtain plasmid pTB1055.

Next, plasmid pTB348 containing hamster dihydrofolic acid reducing enzyme (DHFR) cDNA (described in Japanese Patent Unexamined Publication (Laid-open) No. 61-63282/86) was cleaved with restriction enzymes SalI and HindIII, and a DNA fragment of about 2.6 kb obtained by cleaving plasmid pTB1055 with restriction enzymes SalI and HindIII was ligated thereto, thereby obtaining plasmid pTB1059 (see FIG. 1).

(2) The human NGF-2/NT-3 gene contained in plasmid pHNT2 described in (1) has an ATG sequence in frame in the 5'-upstream (see European Patent Publication No. 386,752). In order to remove this ATG sequence, the following two DNA oligomers were synthesized.

Figure 2:
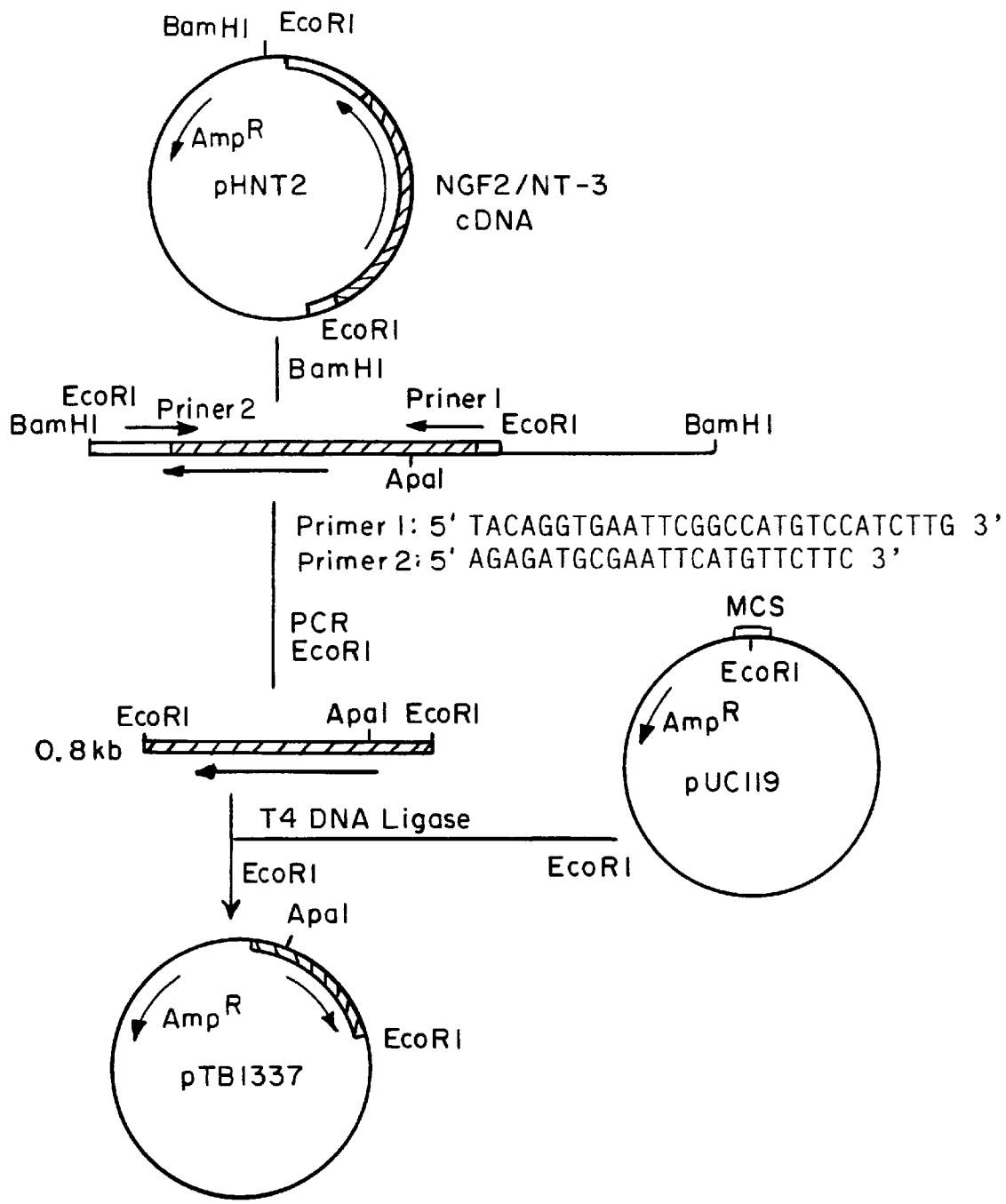
FIGS. 2 and 3 are schematic representations showing the construction of plasmid pTB1339 obtained in Reference Example 4.
Figure 3:
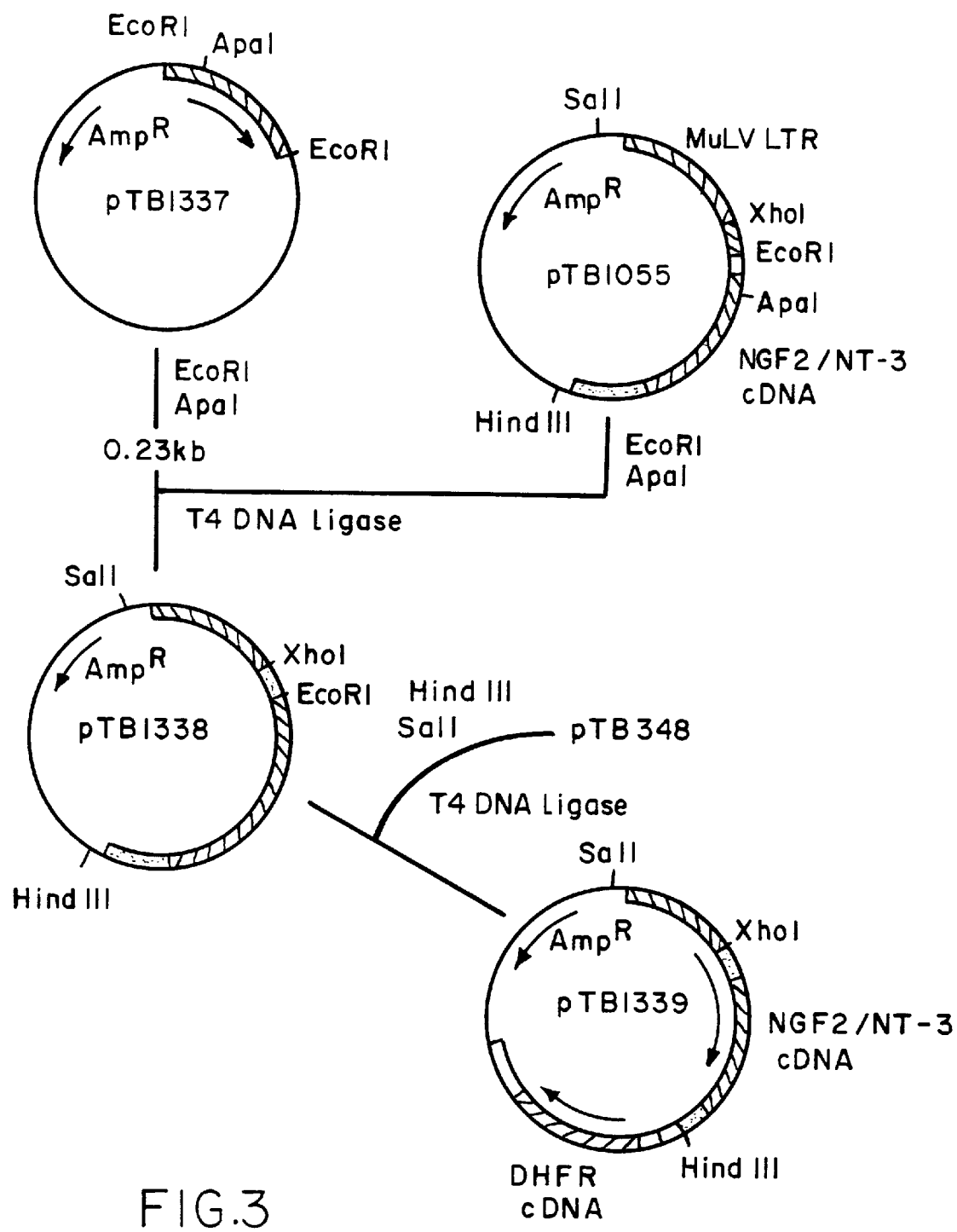

Using primers 1 and 2, polymerase chain reaction (PCR) was conducted through the following procedure. Plasmid pHNT2 was cleaved with restriction enzyme BamHI to obtain a straight-chain fragment. After extraction with phenol, the fragment was extracted with ethanol, evaporated to dryness and dissolved in distilled water. In the PCR, a Gene Amp™ DNA amplifier Makit (Perkin Elmer Thetas, U.S.A.) was used, 0.3 ng of the above-mentioned straight-chain pHNT2 was used as a template DNA, and primers 1 and 2 were each added in an amount of 1.0 μm. The reaction was conducted by repeating 30 times treatments at 94° C. for 1 minute, at 55° C. for 2 minutes and at 72° C. for 3 minutes, using a DNA thermal cycler (Perkin Elmer Thetas, U.S.A.). As a result, a DNA fragment of about 0.8 kb was obtained. Each of primers 1 and 2 had a recognition site for restriction enzyme EcoRI. The resulting fragment was therefore cleaved with EcoRI, and the cleaved fragment was subcloned into the EcoRI site of pUC119. The confirmation of the nucleotide sequence from a single stranded DNA obtained by introducing this recombinant primer pTB1337 into *E. coli* MV1184 strain showed that the gene was amplified correctly for all nucleotide residues. This pTB1377 was cut out with restriction enzymes EcoRI and ApaI to obtain a 0.23-kb DNA fragment. The 0.23-kb DNA fragment was ligated to a DNA fragment of about 4.6 kb which was obtained by cleaving plasmid pTB1055 described in (1) mentioned above with restriction enzymes EcoRI and ApaI to obtain plasmid pTB1338.

pTB1338 was cleaved with restriction enzymes SalI and HindIII, and a hamster DHFR gene was introduced therein in a manner similar to that of (1) described above to obtain expression plasmid pTB1339 (see FIGS. 2 and 3).

DNA coding for the pro region of NGF-2/NT-3 existing on plasmid pTB1339, DNA coding for NGF-2/NT-3 and DNA in the vicinity thereof are shown in FIGS. 7-1 and 7-2 (SEQ ID NO:6).

REFERENCE EXAMPLE 5

Assay of Biological Activity of Human NGF-2/NT-3

A fertilized hen egg was incubated in an incubator at 37.5° C. for 8 to 10 days to develop the embryo, from which the dorsal root ganglion (hereinafter referred to as DRG) was extracted. DRG was treated with a 0.125% trypsin-PBS solution at 37° C. for 20 minutes, and the cells were dispersed by pipetting. The dispersion was suspended in 10% fetal calf serum-Dulbecco's modified MEM medium-50 μg/ml kanamycin, and cultivated in the presence of 5% $CO_2$ at 37° C. for 2 to 4 hours, whereby fibroblasts, etc. were allowed to adhere to a culture dish to fractionate non-adherent cells alone. The non-adherent cells were collected by centrifugation (800 rpm, 5 minutes), and suspended again in 10% fetal calf serum-Dulbecco's modified MEM medium/Ham F-12 medium (mixed at a ratio of 1:1)-1 μM cytosine arabinoside (AraC, Sigma, U.S.A.)-50 μg/ml kanamycin to 10000 cells/ml. A poly-L-ornithine-coated 48-well plate was seeded with 0.5 ml/well of the suspension. A solution to be a sample was added to this medium in an amount of 0.5 to 20 μl, and cultivated in the presence of 5% $CO_2$ at 37° C. for 3 days. Then, the number of viable cells was determined.

REFERENCE EXAMPLE 6

Construction of Human NGF-2/NT-3 Expression Vector

A (-) single stranded DNA was normally prepared by introducing plasmid pHNT5 (the EcoRI inserted fragment of pHNT2 was inserted in the reverse direction) into E. coli MV1183. On the other hand, using plasmid pNGFM108G (see Reference Example 1), a human NGF (-) single stranded DNA was prepared. For these DNAs, oligo 1 and oligo 2 shown below were synthesized.

```
Oligo 1:  5' AGGAGCAAGCGCTCATCATCCCA 3'         (SEQ ID NO:7)

Oligo 2:  5' TCACGGCGGAAGCGCTACGCGGAGCAT 37     (SEQ ID NO:8)
```

Figure 4:
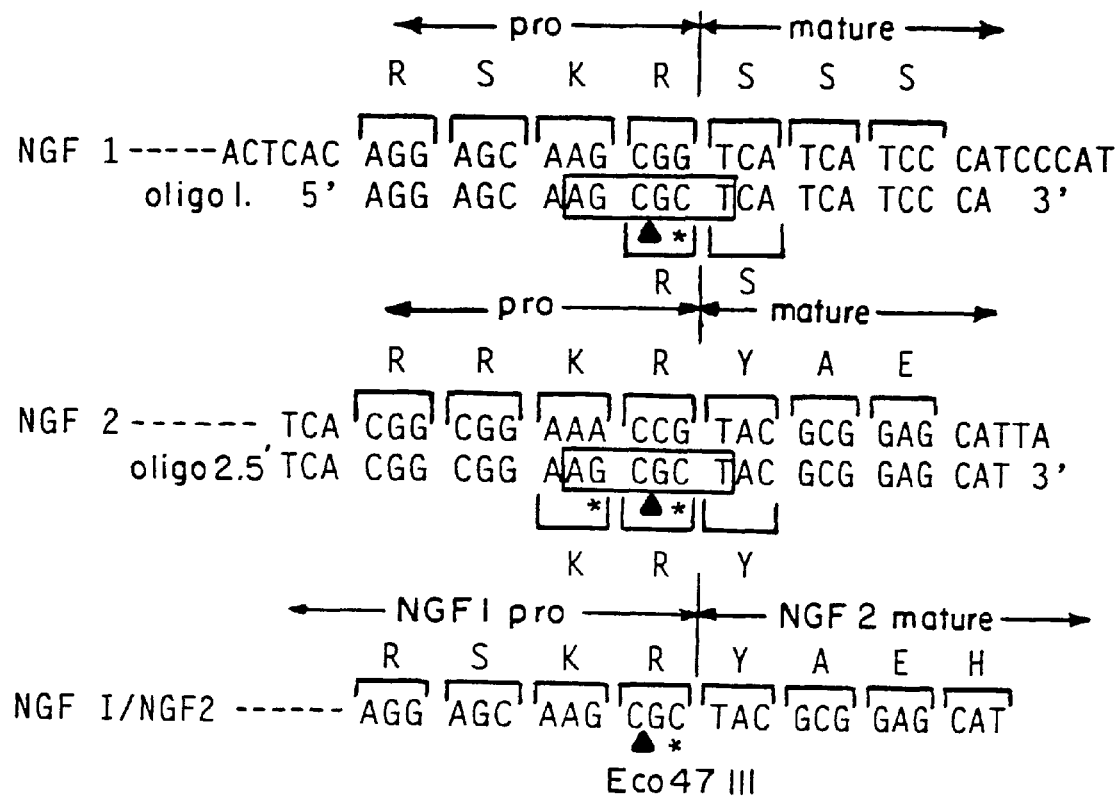
FIGS. 4, 5 and 6 are schematic representations showing the construction of plasmid pTB1344 obtained in Reference Example 6.
Figure 5:
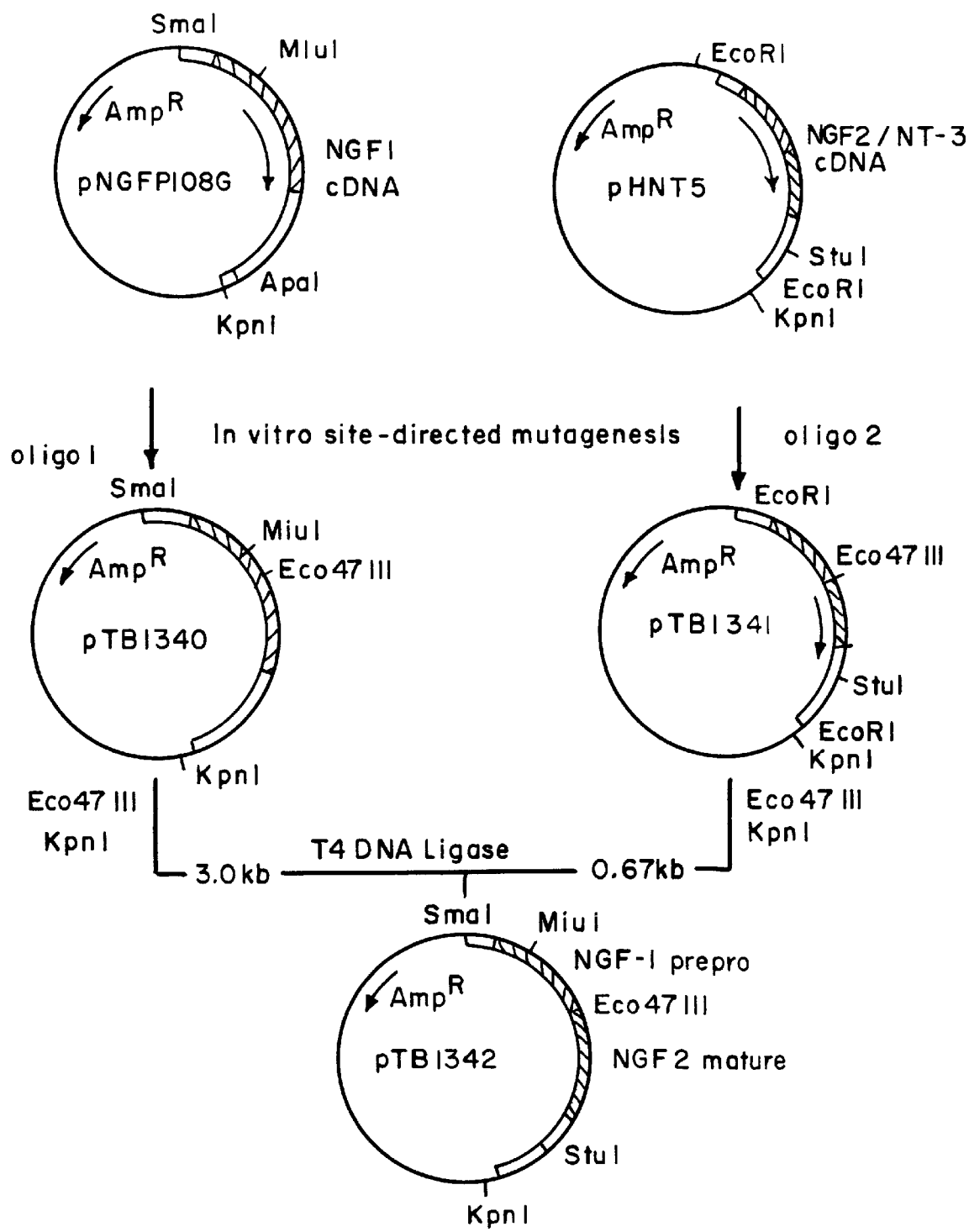
Figure 6:
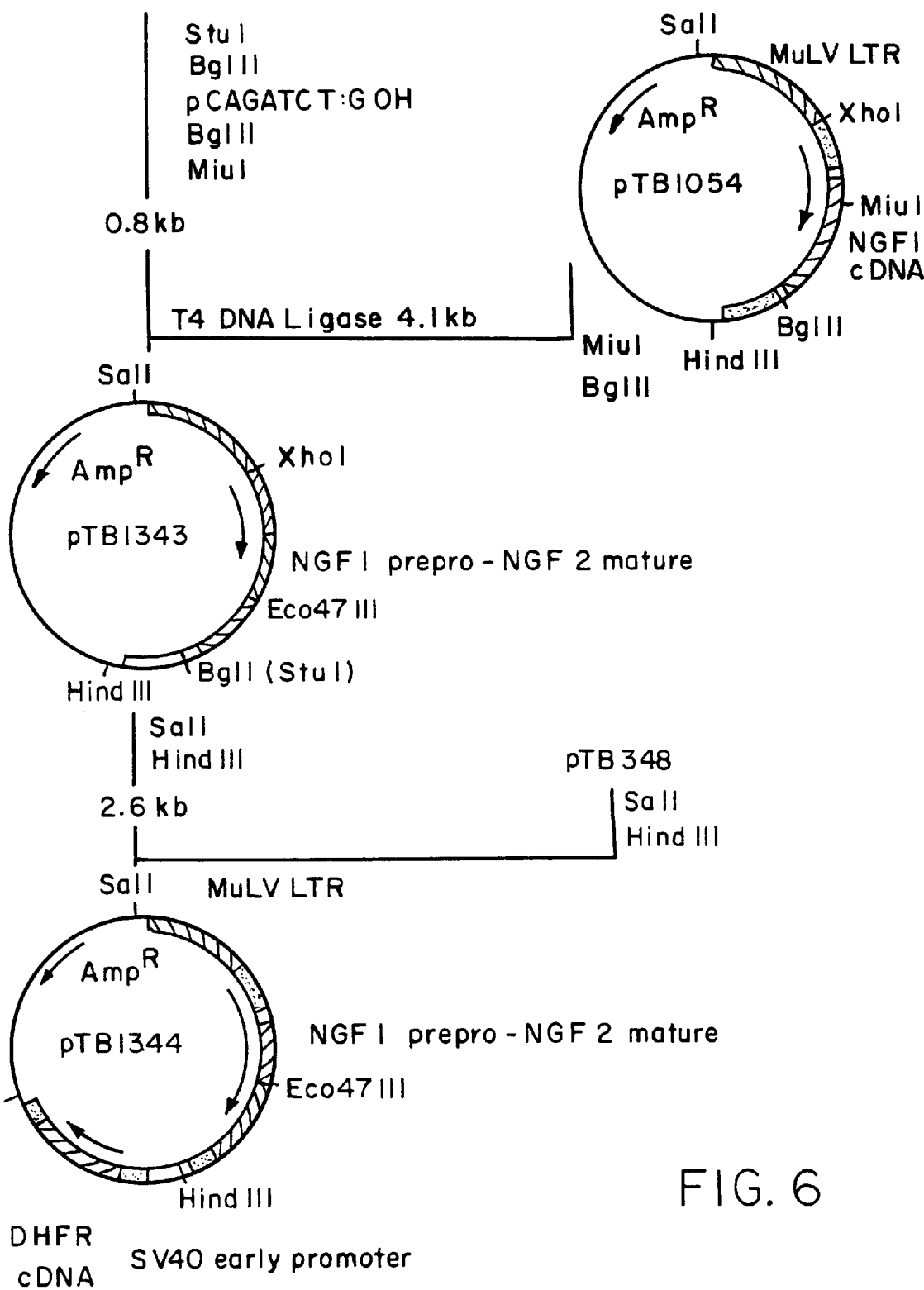

Using these, site-specific nucleotide mutagenesis was introduced to insert the recognition site (AGCGCT) of restriction enzyme Eco47III into each of NGF and NGF-2/NT-3. For this reaction, the in Vitro Mutagenesis System, Ver. 2.0 (Amersham, UK) was used. As a result, plasmid pTB1340 having the Eco47III site in the human NGF gene and plasmid pTB1341 having the Eco47III site in the human NGF-2/NT-3 gene were obtained. pTB1340 was cleaved with restriction enzymes Kpn I and Eco47III, thereby obtaining a DNA fragment of about 3.0 kb. pTB1341 was cleaved with restriction enzymes Kpn I and Eco47III, thereby obtaining a DNA fragment of about 0.67 kb. Both were ligated to each other with T4 DNA ligase to obtain plasmid pTB1342 having a gene for coding a hybrid protein in which the prepro region is NGF and the mature region is NGF-2/NT-3. pTB1342 was cleaved with restriction enzyme StuI, and then, a synthetic BalII linker was ligated thereto. The resulting fragment was cleaved with restriction enzymes MluI and BglII to obtain a 0.8-kb DNA fragment. This fragment was inserted into a DNA fragment of about 4.1 kb obtained by cleaving pTB1054 (see Reference Example 3) with restriction enzymes MluI and BglII to obtain expression plasmid pTB1343 (see FIGS. 4 to 6). This plasmid was further cleaved with SalI and HindIII to obtain a DNA fragment of about 2.6 kb, which was inserted into the SalI-HindIII sites of pTB348, thereby obtaining pTB1344 (see FIGS. 4 to 6).

DNA coding for the pro region of NGF existing on lasmid pTB1344, DNA coding for NGF-2/NT-3 and DNA in the vicinity thereof are shown in FIGS. 8-1 and 8-2 (SEQ ID NO:9).

REFERENCE EXAMPLE 7

Transformation of CHO Cell and Cloning

HamF-12 medium containing 5% fetal calf serum was placed in a Falcon dish (6 cm in diameter), and $4 \times 10^5$ hamster CHO cells (DHFR$^-$) were seeded thereon. After cultivation in the presence of 5% $CO_2$ at 37° C. overnight, the medium was exchanged for the same medium, and cultivation was further continued for 4 hours. Human NGF-2/NT-3 expression plasmids pTB1059, pTB1339 and pTB1344 obtained in Reference Example 1 were each inserted into the CHO cells in an amount of 10 μg per dish by the calcium phosphate method [Graham et al., *Virology*, 52, 456–467 (1973)]. After cultivation for 4 hours, the medium was changed with the fresh medium, and cultivation was conducted overnight. Then, the medium was changed with a selective medium (5% fetal calf serum-Dulbecco's modified MEM-50 μg/ml kanamycin-35 μg/ml proline), and cultivation was continued. After 10 to 15 days, the cells which proliferated as DHFR$^+$ formed a colony, so that they were subjected to single colony isolation and cloned.

REFERENCE EXAMPLE 8

Expression of Human NGF-2/NT-3 Gene in Transformant

A culture supernatant of the CHO transformant obtained by Reference Example 2 was collected, and human NGF-2/NT-3 activity in the culture supernatant was assayed by the method shown in Reference Example 5. As a result, transformation with any of pTB1059, pTB1339 and pTB1344 showed biological activity.

REFERENCE EXAMPLE 9

Establishment of CHO Cell Strain High in Production of Human NGF-2/NT-3

Each of the transformants described in Reference Examples 7 and 8 was cultivated in the selective medium (described in Reference Example 7) containing 100 nM methotrexate. For the clones which survived in this medium, cultivation was continued, further increasing stepwise the concentration of methotrexate in the selective medium. As a result, strain A1002 transformed with plasmid pTB1059, strains CHO-dN2-17 and CHO-dN2-19 transformed with plasmid pTB1339, and strains CHO-N2-1 (IFO 50307, FERM BP-3255) and CHO-N2-37 transformed with plasmid pTB1344 were obtained. The production of NGF-2/NT-3 for these strains was as follows:

| Strain | Production |
|---|---|
| A1002 | 2 μg/L |
| CHO-dN2-17 | 20 μg/L |
| CHO-dN2-19 | 20 μg/L |
| CHO-N2-1 | 100 μg/L |
| CHO-N2-37 | 100 μg/L |

In this table, the product was calculated as a mouse βNGF equivalent by the assay of biological activity described in Reference Example 5. In this example, the limiting dilution point was taken as the 0.02 ng/ml βNGF equivalence point.

REFERENCE EXAMPLE 10

Isolation of Human NGF-2/NT-3

Dulbecco's modified medium containing 5% fetal calf serum, 35 µg/ml proline, 50 µg/ml kanamycin and 2 µM methotrexate was seeded with cell strain CHO-N2-1 obtained in Reference Example 9 at a concentration of $2\times10^4$ cells/cm$^2$, and cultivation was conducted in the presence of 5% $CO_2$ at 37° C. for 7 days. The assay of activity to avian embryo DRG proved that a 10 µg NGF-1 equivalent or more of recombinant human NGF-2/NT-3 was produced in this medium. This culture solution was stored under freezing at −20° C. until use.

One liter of the frozen stored culture supernatant was centrifuged at 8000 rpm at 4° C. for 15 minutes, or filtered (through Toyo Filter No. 2) to remove cell residues. The resulting supernatant was adjusted to final concentrations of 1 mM EDTA and 0.05% CHAPS, and compensated to pH 6.0 with 2N acetic acid. The solution was subjected to centrifugation or filtration again to remove insoluble fractions, and passed through a cation exchange resin. As the cation exchange resin, S-Sepharose First Flow (Pharmacia LKB, Sweden) was used which was equilibrated with 0.1M sodium phosphate buffer (pH 6.0)-1 mM EDTA-0.05% CHAPS and packed into a 2.6 cm diameter, 10 cm high column. The prepared culture supernatant was adsorbed by passing it through this column at 4° C. at a flow rate of 60 ml/hour. After adsorption, the column was washed with 0.1M sodium phosphate buffer (pH 6.0)-1 mM EDTA-0.05% CHAPS at a flow rate of 60 ml/hour for 4 hours, and eluted by allowing to flow 0.5M NaCl-0.1M sodium phosphate buffer (pH 6.0)-1 mM EDTA-0.05% CHAPS at a flow rate of 50 ml/hour. Fractions containing human NGF-2/NT-3 were determined by Western blot analysis using the anti-polypeptide (I) N-terminal peptide antibody described in Reference Example 1 of European Patent Publication No. 386,752, which were collected and concentrated about 20-fold on an Ultrafree 20 (Millipore, U.S.A.). The resulting concentrated solution was purified by gel filtration with a Sephacryl S-100HR (Pharmacia LKB, Sweden) column (1.6 cm in diameter×85 cm) equilibrated with 20 mM Tris-HCl (pH 7.4)-0.15M NaCl-1 mM EDTA-0.05% CHAPS. Human NGF-2/NT-3 fractions were identified by Western blot analysis as described above, and concentrated 20-fold on an Ultrafree 20. The resulting concentrated solution was subjected to reverse-phase HPLC to purify human NGF-2. Namely, this concentrated solution was passed through an Asahipak ODP-50 (Asahi Chemical Industry, Japan) column (8 mm in diameter×150 mm), which was eluted with a linear gradient of 0 to 90% acetonitrile containing 0.1% trifluoroacetic acid (TFA) to obtain about 60 µg of purified human NGF-2/NT-3.

Figure 9:
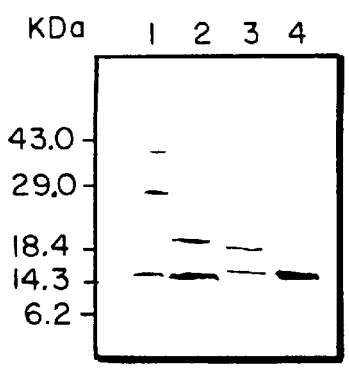
FIG. 9 shows results of SDS-PAGE obtained in Reference Example 10.

The recombinant human NGF-2/NT-3 thus obtained was analyzed by SDS-PAGE (15% (35.1:1)). As a result, it was detected at a molecular weight near 14000 as an approximately homogeneous band (FIG. 9). Further, this was reacted with the antibody shown in Reference Example 1 of European Patent Publication No. 386,752 (FIG. 10).

Figure 10:
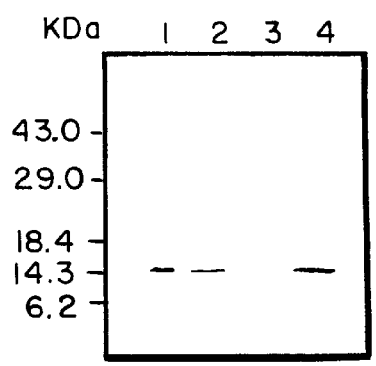
FIG. 10 shows results of SDS-PAGE obtained in Reference Example 10.

FIG. 9 is a diagram showing results of SDS-PAGE analysis of the purification and silver staining, and FIG. 10 is a diagram showing results of Western blot analysis after SDS-PAGE. In both FIGS. 9 and 10, lane 1 indicates the results for polypeptide (I) obtained by the method described in European Patent Publication No. 386,752, lane 2 indicates the results for the sample subjected to reverse-phase chromatography in Reference Example 10, lane 3 indicates the results for fractions not adsorbed to the column in reverse-phase chromatography, and lane 4 indicates the results for the fractions (NGF-2/NT-3 fractions) eluted with a linear gradient of acetonitrile in reverse-phase chromatography.

REFERENCE EXAMPLE 11

Expression of Human NGF-2/NT-3 Gene in Animal Cell

Figure 11:
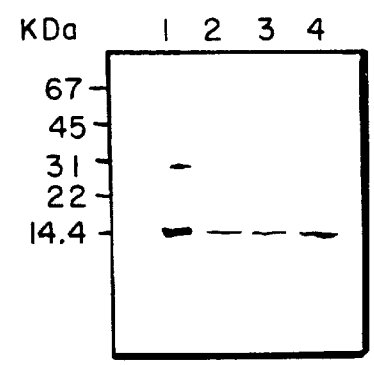
FIG. 11 shows results of SDS-PAGE obtained in Reference Example 11.

For plasmids pTB1059 and pTB1339 obtained in Reference Example 4 and plasmid pTB1344 obtained in Reference Example 1, expression in monkey COS-7 cells was studied. Introduction of the gene was conducted by the calcium phosphate method described in Reference Example 7, with the proviso that 10% fetal calf serum-Dulbecco's modified MEM medium was used as the medium and 0.5% fetal calf serum-Dulbecco's modified MEM medium was used after introduction of the gene. The medium was collected 48 hours after introduction of the gene. To 100 µl of the culture supernatant, 10 µl of 100% (w/v) trichloroacetic acid was added, and the mixture was cooled at 0° C. for 10 minutes, thereby precipitating a protein, which was electrophoresed by SDS-PAGE. Western blot analysis was normally conducted, and a recombinant was detected using the anti-polypeptide (I) N-terminal peptide antibody described in Reference Example 1 of European Patent Publication No. 386,752 (FIG. 11). In this system, pTB1339 most highly produced the recombinant. In FIG. 11, lane 1 indicates the result for polypeptide (I) obtained by the method described in European Patent Publication No. 386,752, lane 2 indicates the result for a COS supernatant according to plasmid pTB1059, lane 3 indicates the result for a COS supernatant according to plasmid pTB1344, and lane 4 indicates the result of a COS supernatant according to plasmid pTB1339.

REFERENCE EXAMPLE 12

Using the CHO-N2-1 strain obtained in Reference Example 9, NGF-2/TN-3 was prepared in large amounts. The preparation method based on the method described in Reference Example 10, but partly modified as follows.

Figure 15:
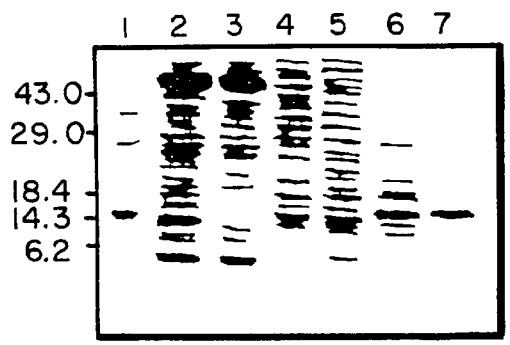
FIG. 15 shows results of SDS-PAGE for products in respective purification procedures, obtained in Reference Example 12.
Figure 16:
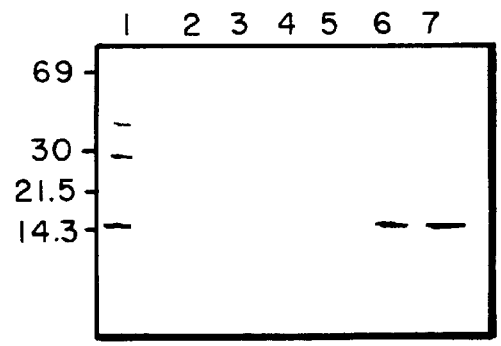
FIG. 16 shows results of SDS-PAGE obtained in Reference Example 12.
Figure 12:
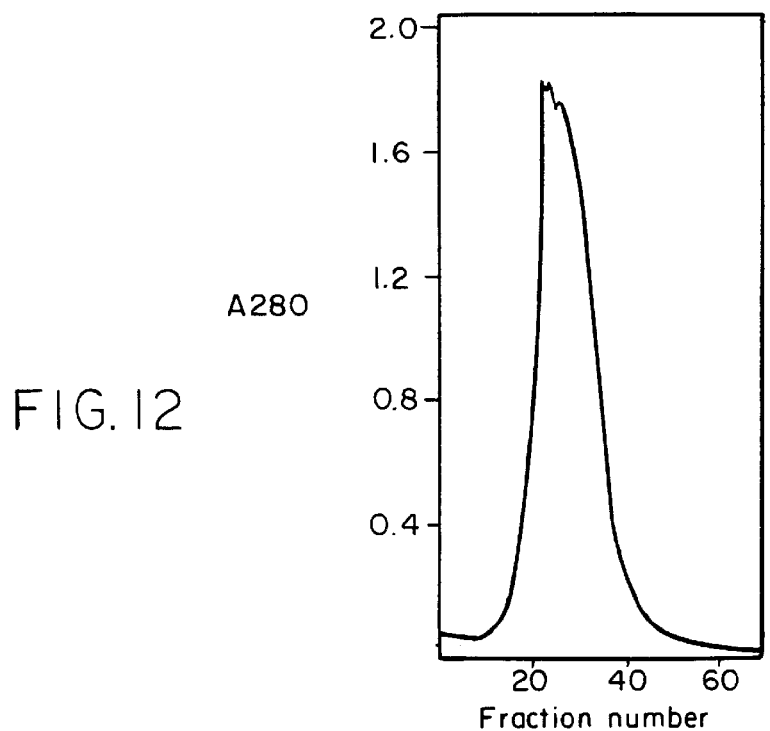
FIG. 12 is a graph showing absorbance for eluted fractions of the culture supernatant of CHO-N2-1 strain on an S-Sepharose column, obtained in Reference Example 12.
Figure 13:
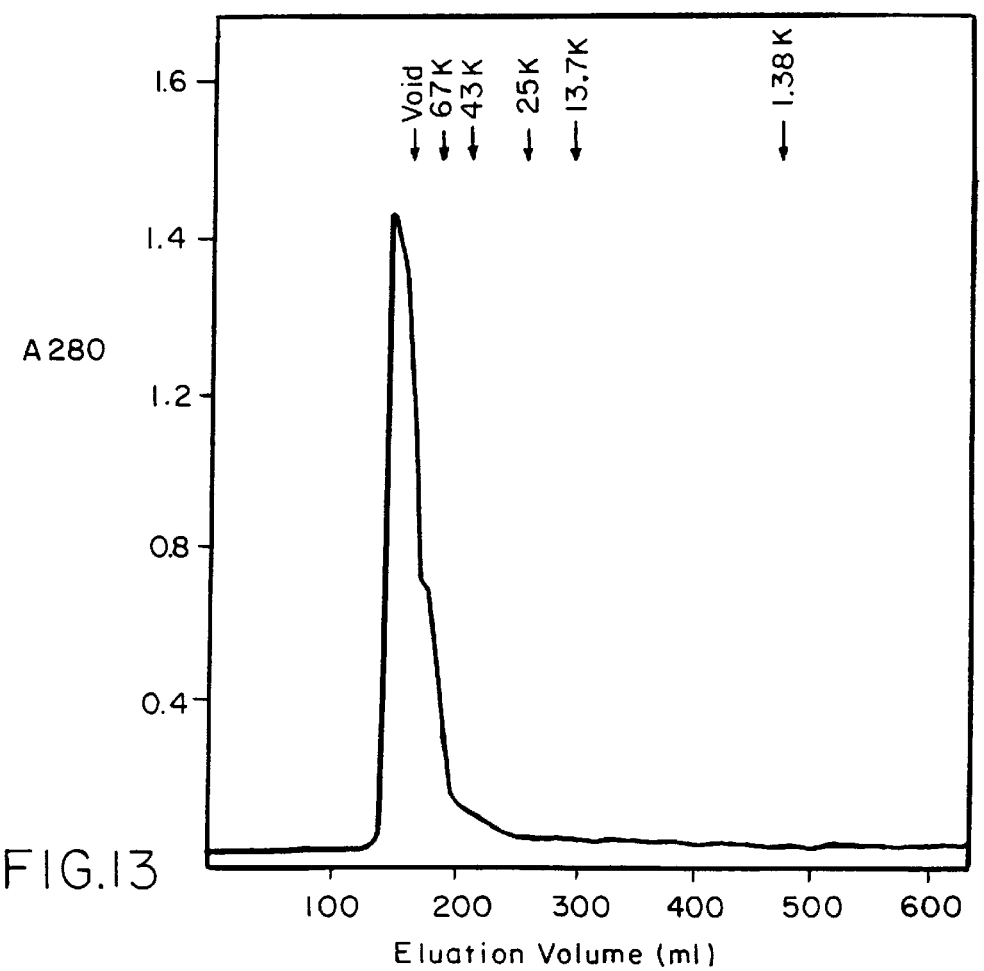
FIG. 13 is a graph showing absorbance for eluted fractions on gel filtration, obtained in Reference Example 12.
Figure 14:
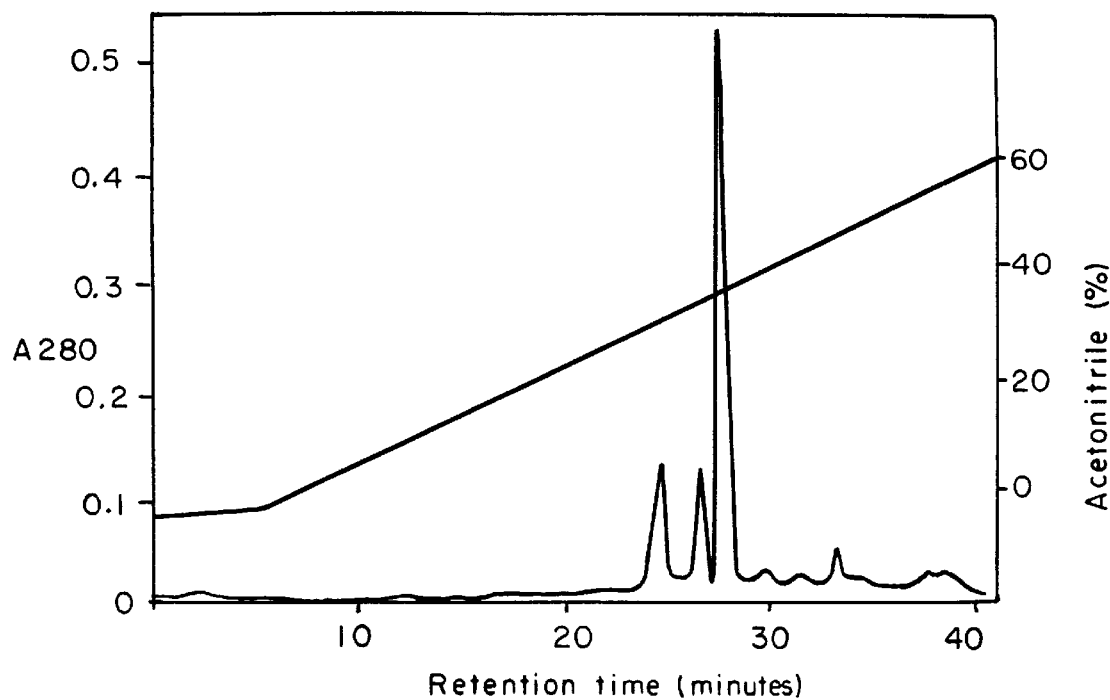
FIG. 14 shows results of reverse-phase chromatogram obtained in Reference Example 12.

Dulbecco's modified MEM medium containing 5% fetal calf serum, 35 µg/ml proline, 50 µg/ml kanamycin and 2 µM methotrexate was seeded with the CHO-N2-1 cell strain at $2\times10^4$ cells/cm$^2$, and cultivation was conducted in the presence of 5% $CO_2$ at 37° C. for 7 days. After collection of the culture supernatant, the medium was changed with Ham F-12 medium/Dulbecco's modified MEM medium containing 5% fetal calf serum, 35 µg/ml proline, 50 µg/ml kanamycin and 2 µM methotrexate (mixed medium of 1:1) (hereinafter briefly referred to as preparation medium), and cultivation was conducted for 3 to 4 days. After collection of the culture supernatant, cultivation was further conducted for 3 to 4 days, followed by collection of a culture supernatant. From hundred and twenty dishes of 10-cm, 5 liters of the culture supernatant was obtained by a series of these cultivation procedures. This was repeated twice to obtain 10 liters of the culture supernatant. The culture supernatant was stored at −20° C. The culture supernatant was treated by the method described in Reference Example 10, and subjected to an S-Sepharose column (5 cm in diameter×20 cm). Active fractions were eluted by the method described in Reference Example 10 to fractionate them by 12 ml/fraction (FIG. 12). Ammonium sulfate was added to this fraction to 50% saturation. After standing at 0° C. for 2 hours, the mixture was centrifuged at 10000 rpm at 4° C. for 15 minutes on a Serval SS34 rotor (U.S.A.) to collect a precipitate. The precipitate was dissolved in 40 ml of 20 mM Tris-HCl (pH 7.4)-1 mM EDTA-0.05% CHAPS. Before gel filtration, the solution was centrifuged at 15000 rpm at 4° C. for 15 minutes on a Serval SS34 rotor to remove insoluble substances. Gel filtration was conducted by the method described in Reference Example 10, with the proviso that a column measured 2.6 cm in diameter×90 cm, the flow rate was 100 ml/hour and the sample amount was 10 ml (FIG. 13). Eluted fractions were concentrated on an Ultrafree 20 (Millipore, U.S.A.). The resulting concentrated solution was subjected to reverse-phase chromatography according to the method described in Reference Example 10 (1 ml/fraction) (FIG. 14). Table 1 shows the summary of the purification procedures. Diagrams of SDS-PAGE analysis for these are shown in FIGS. 15 and 16. The final sample exhibited an approximately homogeneous band. The above results proved that 210 µg of the recombinant sample was obtained from about 10 liters of the culture supernatant.

FIG. 15 shows results of silver staining, and FIG. 16 shows results of Western blot analysis. In FIGS. 15 and 16, lane 1 indicates the results for 0.01 µg of polypeptide (I) obtained by the method described in European Patent Publication No. 386,752, lane 2 indicates the results for 10 µg of the culture supernatant of the CHO-N2-1 cells, lane 3 indicates the results for 10 µg of fractions not adsorbed to S-Sepharose, lane 4 indicates the results for 1 µg of the fractions eluted on S-Sepharose, lane 5 indicates the results for 1 µg of the ammonium sulfate-precipitated fraction, lane 6 indicates the results for 0.1 µg of the fractions eluted by gel filtration, and lane 7 indicates the results for 0.1 µg of the fractions eluted by reverse-phase HPLC.

Western blotting (FIG. 16) and silver staining (FIG. 17) are shown together to indicate that the sample is finally purified to a purity of 95% or more from a purity of about 0.001 to 0.01% of total proteins at early stage (an efficiency of $10^4$ times).

TABLE 1

| | Volume (ml) | Conc. of protein (mg/ml) | *1 Amount of protein (mg) | *2 Biological activity (µg eq.) | Yield (%) |
|---|---|---|---|---|---|
| Culture supernatant | 9500 | 1.15 | 10900 | 126 | 100 |
| S-Sepharose | | | | | |
| Flow through fraction | 9500 | 1.12 | 10600 | 15 | 12 |
| 0.5 M NaCl-eluted fraction | 325 | 2.00 | 700 | 49 | 38 |
| Ammonium sulfate precipitate (precipitated fraction) | 40 | 11.3 | 452 | 55 | 43 |
| Sephacryl S-100 HR (concentrated fraction) | 2.5 | 0.20 | 0.50 | 33 | 26 |
| Reverse-phase HPLC | 1.0 | 0.21 | 0.21 | 25 | 19 |

*1: Determined by the Bradford method.
*2: Shown by a human NGF equivalent based on neurite outgrowth to DRG.

REFERENCE EXAMPLE 13

Biological Activity of Purified Recombinant (I)

Figure 17:
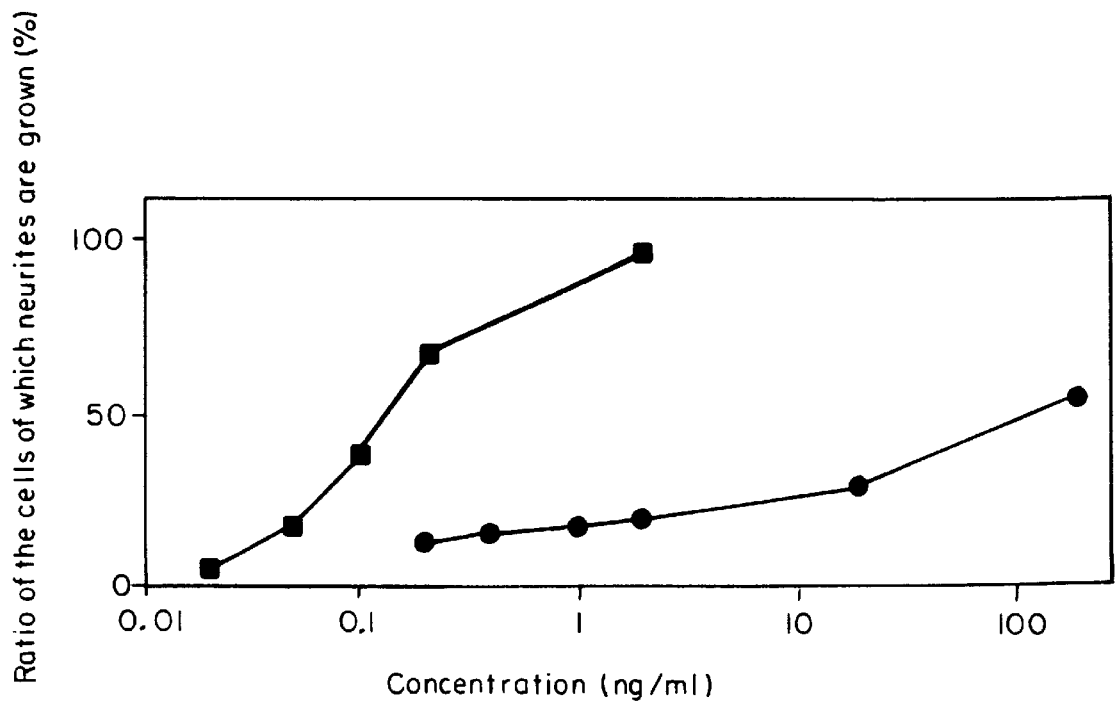
FIG. 17 shows results of assay for biological activity tested in Reference Example 13.

For the final purified sample obtained in Reference Example 12, biological activity was assayed by the method described in Reference Example 5. As a control, mouse βNGF (Wako Pure Chemical Industries, Japan) was used. Results thereof are shown in FIG. 17. In FIG. 17, filled squares indicate the result for mouse βNGF, and filled circles indicate the result for NGF-2/NT-3. As is shown in FIG. 17, NGF-2/NT-3 is lower in activity than βNGF in this system.

REFERENCE EXAMPLE 14

Biological Activity of Purified Recombinant (II)

Figure 18:
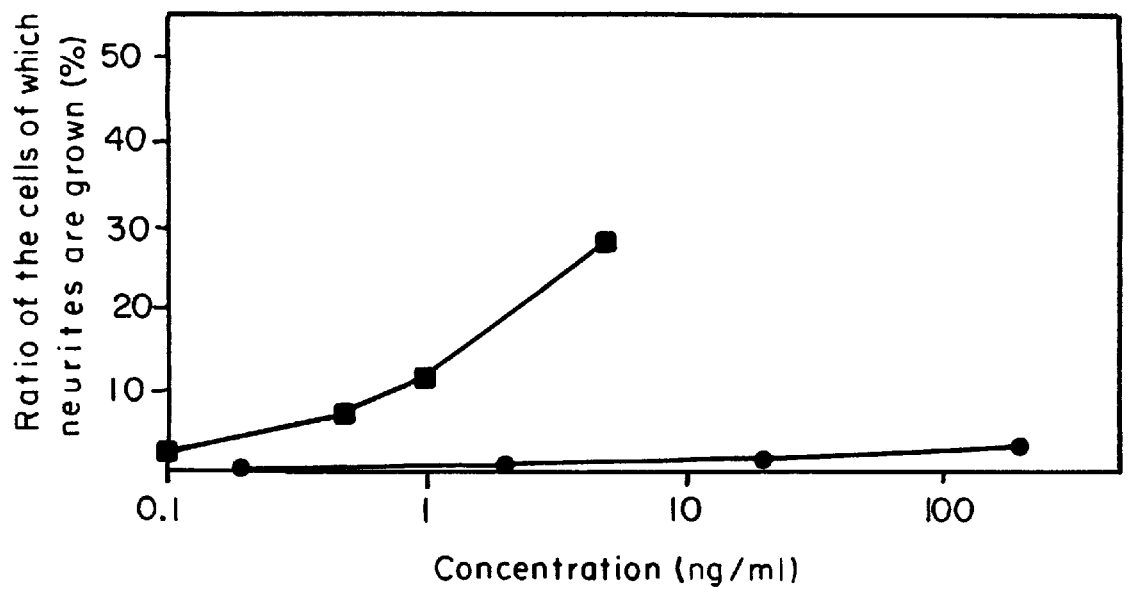
FIG. 18 shows results of assay for biological activity tested in Reference Example 14.

Biological activity to rat PC12 cells was assayed according to the method described in *Biochem. Biophys. Res. Commun.*, 171, 116–122 (1990). Results thereof are shown in FIG. 18. In FIG. 18, filled squares indicate the result for mouse βNGF, and filled circles indicate the result for NGF-2/NT-3. FIG. 18 reveals that recombinant NGF-2/NT-3 is very low in activity of inducing neurite outgrowth to the PC12 cells and the activity is $1/10^3$ or less that of mouse βNGF (Wako Pure Chemical Industries).

REFERENCE EXAMPLE 15

The CHO-N2-1 strain obtained in Reference Example 9 was seeded and cultivated as with Reference Example 10. The medium was changed with a serum-free medium (Cosmedium, Cosmobio), and cultivation was conducted for an additional 2 days. One liter of the culture supernatant was collected from 100 10-cm dishes. 0.5 mM PMSF and 1 mM benzamidine were added to the collected culture supernatant and buffer of a column to purify NGF-2/NT-3 in a manner similar to that of Reference Example 10. Reverse-phase HPLC gave three peaks at retention times of 24 minutes (P1), 26 minutes (P2) and 28 minutes (P3) (FIG. 19).

Figure 20:
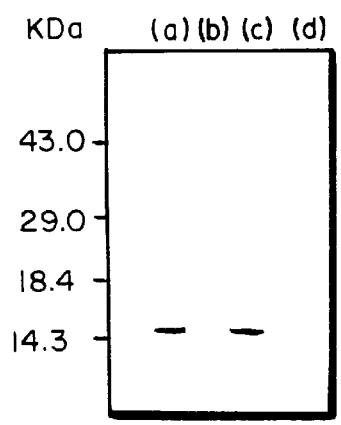
FIG. 20 shows results of Western blot analysis obtained in Reference Example 15.
Figure 21:
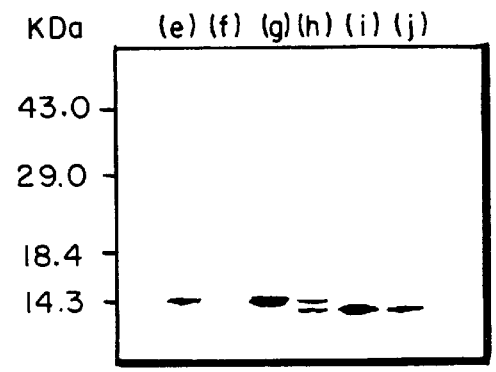
FIG. 21 shows results of SDS-PAGE obtained in Reference Example 15.

P2 and P3 had biological activity to the avian embryo DRG nerve, but P1 did not have the activity. The P2 protein moved in PAGE concurrently with recombinant NGF-2 produced by *E. coli*, but the P3 protein moved a little faster than those (FIG. 21). Only the P2 protein recognized the anti-polypeptide (I) N-terminal peptide antibody described in Reference Example 2 of European Patent Publication No. 386,752 (FIG. 20). In FIG. 20, lane (a) indicates the result for NGF-2 produced by the *E. coli* transformant, lane (b) to (d) respectively indicates the result for fraction 24 (P1), fraction 26 (P2) and fraction 28 (P3) obtained by reverse-phase HPLC (FIG. 19).

Figure 19:
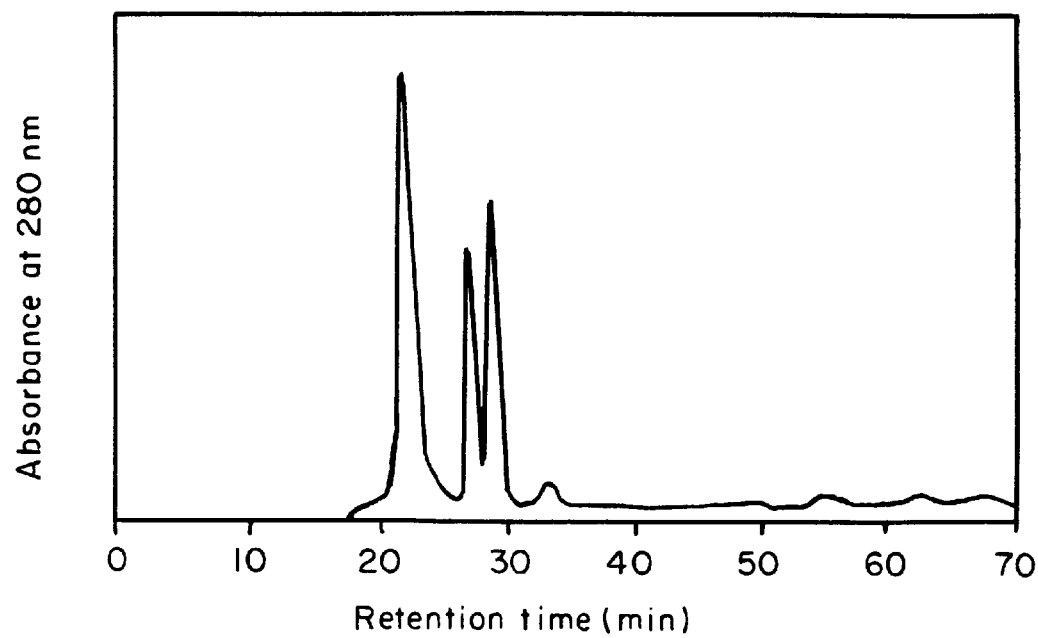
FIG. 19 shows results of reverse-phase chromatogram obtained in Reference Example 15.

In FIG. 21, lane (e) indicates the result for NGF produced by the *E. coli* transformant, lane (f) to (j) respectively indicates the result for fraction 25, fraction 26 (P2), fraction 27, fraction 28 (P3) and fraction 29 obtained by reverse-phase HPLC (FIG. 19).

Analysis of N-terminal amino acids showed that the N-terminal sequence of P2 was identified with that of mature NGF-2/NT-3 and P3 corresponded to N-terminal five residue-deleted NGF-2/NT-3 (Table 2).

TABLE 2

| Cycle | P2 | P3 | Amino acid sequence deduced from cDNA |
|---|---|---|---|
| 1 | Tyr | Ser | Tyr |
| 2 | Ala | His | Ala |
| 3 | Glu | Arg | Glu |
| 4 | His | Gly | His |
| 5 | Lys | Glu | Lys |
| 6 | Ser | Tyr | Ser |
| 7 | His | Ser | His |
| 8 | Arg | Val | Arg |
| 9 | Gly | — | Gly |

TABLE 2-continued

| Cycle | P2 | P3 | Amino acid sequence deduced from cDNA |
|---|---|---|---|
| 10 | Glu | Asp | Glu |
| 11 | ND | Ser | Tyr |
| 12 | ND | Glu | Ser |
| 13 | ND | Ser | Val |
| 14 | ND | Leu | Cys |
| 15 | ND | Trp | Asp |

ND: Not determined.

EXAMPLE 1

Effect of NGF-2/NT-3 on Human Peripheral Blood Lymphocyte

The human peripheral blood collected from the human vein was stratified on a lymphocyte separating medium (LSM, Organon teknika Corp.), and subjected to centrifugation at 2000 rpm at room temperature for 30 minutes. An interfacial opaque layer formed of the lymphocytes was collected, and suspended in RPMI 1640 medium. Centrifugation at 1500 rpm for 5 minutes was repeated twice for washing. The resulting lymphocyte fraction was suspended in RPMI 1640 medium, and seeded on a plastic dish previously coated with fetal calf serum (FCS). After incubation in a 5% $CO_2$ incubator at 37° C. for 1 hour, non-adherent cells were collected, and washed with RPMI 1640 medium. The human peripheral blood-derived lymphocyte cells thus obtained were suspended in each of agar media (RPMI 1640 media containing 0.3% bactoagar and 20% FCS) each containing 5, 50 and 500 U/ml of human GM-CSF (recombinant, Genzyme) or 5, 50 and 500 ng/ml of human NGF [recombinant, *Biochem. Biophys. Res. Commun.*, 171, 116 (1990)] or 5, 50 and 500 ng/ml of N-terminal five amino acid residues-deleted NGF-2/NT-3 obtained in Reference Example 12 described ($1 \times 10^6$ cells/ml), and each 35-mm dish was seeded with 1 ml of the suspension. After solidification of agar, cultivation was conducted in a $CO_2$ incubator (5% $CO_2$) at 37° C. for 2 weeks. Then, the number of colonies in which the number of cells reached 50 or more was counted.

Figure 23:
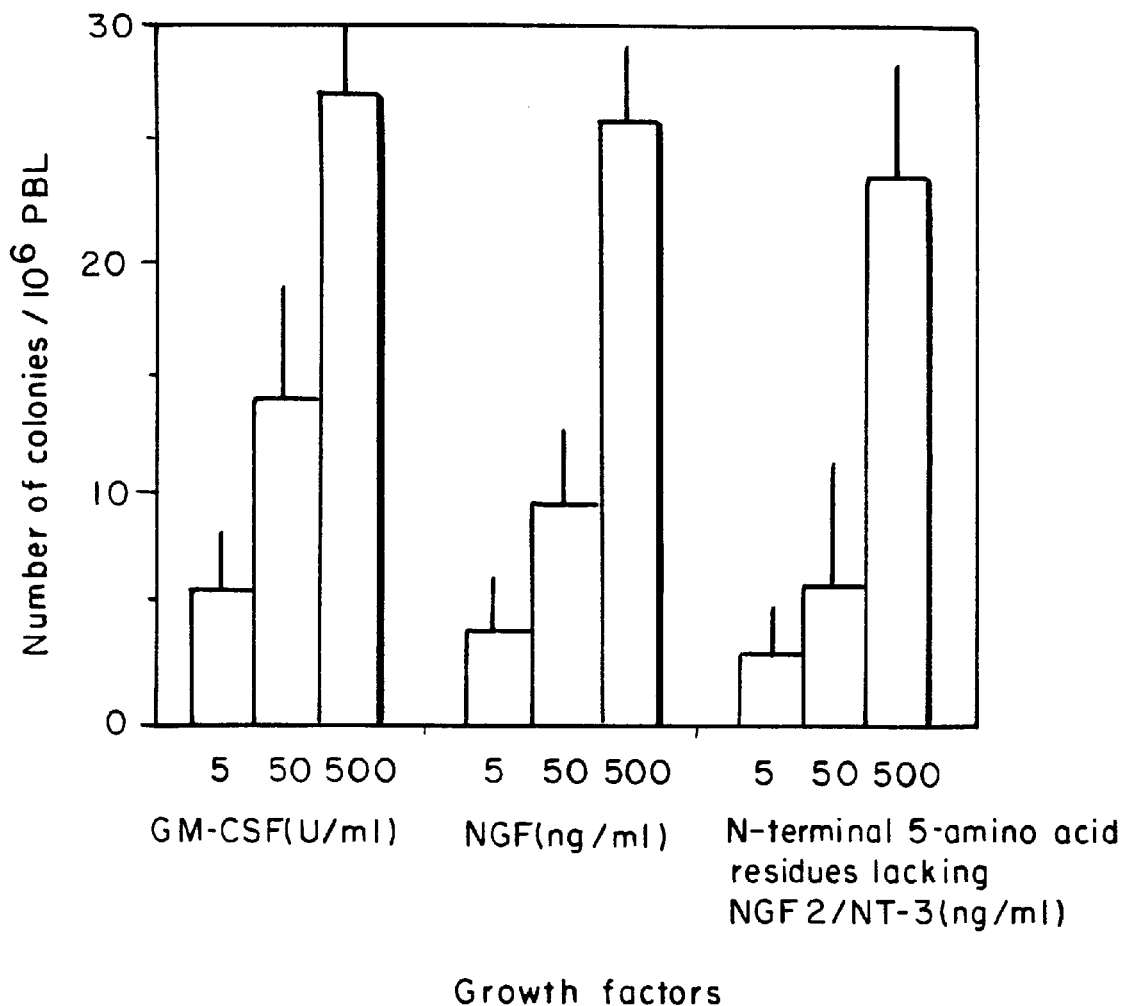
FIG. 23 shows an effect of N-terminal five amino acid residues-deleted NGF-2/NT-3 on the human peripheral blood lymphocytes, obtained in Example 1.

Results thereof are shown in FIG. 23. As apparent from FIG. 23, the colony formation of the human peripheral blood lymphocytes was obviously promoted by addition of N-terminal five amino acid residues-deleted NGF-2/NT-3 (6th to 119th amino acid residues in SEQ ID NO:12), as is the case with addition of GM-CSF or NGF.

EXAMPLE 2

Preparation of Injection

An aqueous solution (pH 7.4) containing 0.5 mg/ml of N-terminal five amino acid residues-deleted NGF-2/NT-3 (6th to 119th amino acid residues in SEQ ID NO:12) obtained in Reference Example 12, 10 mg/ml of sucrose and 15 mg/ml of sodium citrate is prepared to obtain a stable injection

What is claimed is:

1. A method of treating neutropenia in a mammal which comprises administering to said mammal a pharmaceutical composition comprising a blood cell increasing amount of nerve growth factor-2.

2. The method as claimed in claim 1 wherein nerve growth factor-2 is a recombinant one.

3. The method as claimed in claim 1 wherein nerve growth factor-2 is a polypeptide as defined by (i) SEQ ID NO:12 or (ii) the sequence of 1st to 118th amino acid residues as defined by SEQ ID NO:12.

4. The method as claimed in claim 1 wherein nerve growth factor-2 is a polypeptide as defined by (i) SEQ ID NO:12 or (ii) the sequence of 1st to 118th amino acid residues as defined by SEQ ID NO:12, which polypeptide further comprises Met at the N-terminus.

5. The method as claimed in claim 1 wherein nerve growth factor-2 is a mixture of
   (A) a polypeptide as defined by (i) SEQ ID NO:12 or (ii) the sequence of 1st to 118th amino acid residues as defined by SEQ ID NO:12 and
   (B) a polypeptide as defined by (i) SEQ ID NO:12 or (ii) the sequence of 1st to 118th amino acid residues as defined by SEQ ID NO:12, which polypeptide further comprises Met at the N-terminus.

6. The method as claimed in claim 1 wherein nerve growth factor-2 is a variant of a polypeptide as defined by (i) SEQ ID NO:12 or (ii) the sequence of 1st to 118th amino acid residues as defined by SEQ ID NO:12, wherein the variant is a substitution, deletion or addition variant.

7. The method as claimed in claim 6 wherein the variant of nerve growth factor-2 is a fragment lacking one or more amino acid residues from the amino terminus of a polypeptide as defined by (i) SEQ ID NO:12 or (ii) the sequence of 1st to 118th amino acid residues as defined by SEQ ID NO:12.

8. The method as claimed in claim 7 wherein the variant of nerve growth factor-2 is a fragment lacking 5 amino acid residues from the amino terminus of a polypeptide as defined by (i) SEQ ID NO:12 or (ii) the sequence of 1st to 118th amino acid residues as defined by SEQ ID NO:12.

9. The method as claimed in claim 7 wherein the variant of nerve growth factor-2 is a polypeptide in which the constituent amino acid residues of a polypeptide, as defined by (i) SEQ ID NO:12 or (ii) the sequence of 1st to 118th amino acid residues as defined by SEQ ID NO:12 is partially lacking or substituted by other amino acids.

10. The method as claimed in claim 1 wherein the nerve growth factor-2 is human nerve growth factor-2.

11. A method of treating mammalian neutropenia which comprises administering to a mammal a pharmaceutical composition comprising a pharmaceutically-acceptable carrier containing a peripheral differentiated blood cell increasing effective amount of (A) a human nerve growth factor-2 or (B) a substitution, deletion or addition mutein thereof.

12. A method of treating mammalian neutropenia which comprises administering to a mammal a pharmaceutical composition comprising a pharmaceutically-acceptable carrier containing a peripheral differentiated blood cell increasing effective amount of (A) a human nerve growth factor-2 or (B) a substitution, deletion or addition mutein thereof, wherein said human nerve growth factor-2 is defined by (i) SEQ ID NO: 12, (ii) the sequence of 1st to 118th amino acid residues as defined by SEQ ID NO: 12, (iii) the sequence of 1st to 118th amino acid residues as defined by SEQ ID NO: 12 and having Met at the N-terminus, or (iv) the amino acid sequence wherein 5 amino acid residues are deleted from the amino terminus of the sequence of (i) or (ii).

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:1:

AGCTTGCCGC CACCATGTCC ATGTTGTTCT ACACTCT                                37

(2) INFORMATION FOR SEQ ID NO:2:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Other nucleic acid,  Synthetic DNA (xi) SEQUENCE DESCRIPTION: SEQ ID NO:2:

GATCAGAGTG TAGAACAACA TGGACATGGT GGCGGCA                                37

(2) INFORMATION FOR SEQ ID NO:3:

(i) SEQUENCE CHARACTERISTICS:

(A) LENGTH: 12 base pairs
            (B) TYPE: nucleic acid
            (C) STRANDEDNESS: single
            (D) TOPOLOGY: linear (ii) MOLECULE TYPE: Other nucleic acid, Synthetic DNA (xi) SEQUENCE DESCRIPTION: SEQ ID NO:3:

CAGATCTGGG CC                                                         12

(2) INFORMATION FOR SEQ ID NO:4:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: Other nucleic acid, Synthetic DNA (xi) SEQUENCE DESCRIPTION: SEQ ID NO:4:

TACAGGTGAA TTCGGCCATG TCCATCTTG                                       29

(2) INFORMATION FOR SEQ ID NO:5:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Other nucleic acid, Synthetic DNA (xi) SEQUENCE DESCRIPTION: SEQ ID NO:5:

AGAGATGCGA ATTCATGTTC TTC                                             23

(2) INFORMATION FOR SEQ ID NO:6:

(i) SEQUENCE CHARACTERISTICS:
            (A) LENGTH: 969 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Homo sapiens (ix) FEATURE:
            (A) NAME/KEY: CDS
            (B) LOCATION: 11..781

(ix) FEATURE:
            (A) NAME/KEY: sig_peptide
            (B) LOCATION: 11..67

(ix) FEATURE:
            (A) NAME/KEY: mat_peptide
            (B) LOCATION: 425..781

(xi) SEQUENCE DESCRIPTION: SEQ ID NO:6:

GAATTCGGCC ATG TCC ATC TTG TTT TAT GTG ATA TTT CTC GCT TAT CTC         49
           Met Ser Ile Leu Phe Tyr Val Ile Phe Leu Ala Tyr Leu
           -138          -135              -130

CGT GGC ATC CAA GGT AAC AAC ATG GAT CAA AGG AGT TTG CCA GAA GAC        97
Arg Gly Ile Gln Gly Asn Asn Met Asp Gln Arg Ser Leu Pro Glu Asp
-125             -120             -115                 -110

TCG CTC AAT TCC CTC ATT ATT AAG CTG ATC CAG GCA GAT ATT TTG AAA       145
Ser Leu Asn Ser Leu Ile Ile Lys Leu Ile Gln Ala Asp Ile Leu Lys
             -105                 -100                 -95

```
AAC AAG CTC TCC AAG CAG ATG GTG GAC GTT AAG GAA AAT TAC CAG AGC         193
Asn Lys Leu Ser Lys Gln Met Val Asp Val Lys Glu Asn Tyr Gln Ser
            -90                 -85                 -80

ACC CTG CCC AAA GCT GAG GCT CCC CGA GAG CCG GAG CGG GGA GGG CCC         241
Thr Leu Pro Lys Ala Glu Ala Pro Arg Glu Pro Glu Arg Gly Gly Pro
            -75                 -70                 -65

GCC AAG TCA GCA TTC CAG CCA GTG ATT GCA ATG GAC ACC GAA CTG CTG         289
Ala Lys Ser Ala Phe Gln Pro Val Ile Ala Met Asp Thr Glu Leu Leu
            -60                 -55                 -50

CGA CAA CAG AGA CGC TAC AAC TCA CCG CGG GTC CTG CTG AGC GAC AGC         337
Arg Gln Gln Arg Arg Tyr Asn Ser Pro Arg Val Leu Leu Ser Asp Ser
-45                 -40                 -35                 -30

ACC CCC TTG GAG CCC CCG CCC TTG TAT CTC ATG GAG GAT TAC GTG GGC         385
Thr Pro Leu Glu Pro Pro Pro Leu Tyr Leu Met Glu Asp Tyr Val Gly
            -25                 -20                 -15

AGC CCC GTG GTG GCG AAC AGA ACA TCA CGG CGG AAA CGG TAC GCG GAG         433
Ser Pro Val Val Ala Asn Arg Thr Ser Arg Arg Lys Arg Tyr Ala Glu
            -10                  -5                   1

CAT AAG AGT CAC CGA GGG GAG TAC TCG GTA TGT GAC AGT GAG AGT CTG         481
His Lys Ser His Arg Gly Glu Tyr Ser Val Cys Asp Ser Glu Ser Leu
  5                  10                  15

TGG GTG ACC GAC AAG TCA TCG GCC ATC GAC ATT CGG GGA CAC CAG GTC         529
Trp Val Thr Asp Lys Ser Ser Ala Ile Asp Ile Arg Gly His Gln Val
 20                  25                  30                  35

ACG GTG CTG GGG GAG ATC AAA ACG GGC AAC TCT CCC GTC AAA CAA TAT         577
Thr Val Leu Gly Glu Ile Lys Thr Gly Asn Ser Pro Val Lys Gln Tyr
             40                  45                  50

TTT TAT GAA ACG CGA TGT AAG GAA GCC AGG CCG GTC AAA AAC GGT TGC         625
Phe Tyr Glu Thr Arg Cys Lys Glu Ala Arg Pro Val Lys Asn Gly Cys
             55                  60                  65

AGG GGT ATT GAT GAT AAA CAC TGG AAC TCT CAG TGC AAA ACA TCC CAA         673
Arg Gly Ile Asp Asp Lys His Trp Asn Ser Gln Cys Lys Thr Ser Gln
             70                  75                  80

ACC TAC GTC CGA GCA CTG ACT TCA GAG AAC AAT AAA CTC GTG GGC TGG         721
Thr Tyr Val Arg Ala Leu Thr Ser Glu Asn Asn Lys Leu Val Gly Trp
             85                  90                  95

CGG TGG ATA CGG ATA GAC ACG TCC TGT GTG TGT GCC TTG TCG AGA AAA         769
Arg Trp Ile Arg Ile Asp Thr Ser Cys Val Cys Ala Leu Ser Arg Lys
100                 105                 110                 115

ATC GGA AGA ACA TGAATTGGCA TCTCTCCCCA TATATAAATT ATTACTTTAA             821
Ile Gly Arg Thr

ATTATATGAT ATGCATGTAG CATATAAATG TTTATATTGT TTTTATATAT TATAAGTTGA       881

CCTTTATTTA TTAAACTTCA GCAACCCTAC AGTATATAGG CTTTTTTCTC AATAAAATCA       941

GTGTGCTTGC CTTCCCTCAG GCAGATCT                                          969

(2) INFORMATION FOR SEQ ID NO:7:

(i) SEQUENCE CHARACTERISTICS:
        (A) LENGTH: 257 amino acids
        (B) TYPE: amino acid
        (D) TOPOLOGY: linear (ii) MOLECULE TYPE: protein (xi) SEQUENCE DESCRIPTION: SEQ ID NO:7:

Met Ser Ile Leu Phe Tyr Val Ile Phe Leu Ala Tyr Leu Arg Gly Ile
-138            -135                -130                -125

Gln Gly Asn Asn Met Asp Gln Arg Ser Leu Pro Glu Asp Ser Leu Asn
        -120                -115                -110
```

```
Ser Leu Ile Ile Lys Leu Ile Gln Ala Asp Ile Leu Lys Asn Lys Leu
    -105            -100              -95              
Ser Lys Gln Met Val Asp Val Lys Glu Asn Tyr Gln Ser Thr Leu Pro
-90             -85             -80              -75
Lys Ala Glu Ala Pro Arg Glu Pro Glu Arg Gly Gly Pro Ala Lys Ser
            -70             -65             -60
Ala Phe Gln Pro Val Ile Ala Met Asp Thr Glu Leu Leu Arg Gln Gln
        -55             -50              -45
Arg Arg Tyr Asn Ser Pro Arg Val Leu Leu Ser Asp Ser Thr Pro Leu
        -40             -35             -30
Glu Pro Pro Pro Leu Tyr Leu Met Glu Asp Tyr Val Gly Ser Pro Val
    -25             -20              -15
Val Ala Asn Arg Thr Ser Arg Arg Lys Arg Tyr Ala Glu His Lys Ser
-10             -5                   1               5
His Arg Gly Glu Tyr Ser Val Cys Asp Ser Glu Ser Leu Trp Val Thr
            10              15              20
Asp Lys Ser Ser Ala Ile Asp Ile Arg Gly His Gln Val Thr Val Leu
        25              30              35
Gly Glu Ile Lys Thr Gly Asn Ser Pro Val Lys Gln Tyr Phe Tyr Glu
    40              45              50
Thr Arg Cys Lys Glu Ala Arg Pro Val Lys Asn Gly Cys Arg Gly Ile
55              60              65              70
Asp Asp Lys His Trp Asn Ser Gln Cys Lys Thr Ser Gln Thr Tyr Val
            75              80              85
Arg Ala Leu Thr Ser Glu Asn Asn Lys Leu Val Gly Trp Arg Trp Ile
            90              95              100
Arg Ile Asp Thr Ser Cys Val Cys Ala Leu Ser Arg Lys Ile Gly Arg
            105             110             115
Thr (2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:8:

TCACGGCGGA AGCGCTACGC GGAGCAT                                27

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:9:

AGGAGCAAGC GCTCATCATC CCA                                    23

(2) INFORMATION FOR SEQ ID NO:10:

(i) SEQUENCE CHARACTERISTICS:
        (A) LENGTH: 923 base pairs
        (B) TYPE: nucleic acid
```

(C) STRANDEDNESS: double
(D) TOPOLOGY: linear (ii) MOLECULE TYPE: DNA (genomic)

(ix) FEATURE:
    (A) NAME/KEY: CDS
    (B) LOCATION: 16..735

(ix) FEATURE:
    (A) NAME/KEY: sig_peptide
    (B) LOCATION: 16..69

(ix) FEATURE:
    (A) NAME/KEY: mat_peptide
    (B) LOCATION: 379..735

(xi) SEQUENCE DESCRIPTION: SEQ ID NO:10:

```
TAGCTTGCCG CCACC ATG TCC ATG TTG TTC TAC ACT CTG ATC ACA GCT TTT        51
                 Met Ser Met Leu Phe Tyr Thr Leu Ile Thr Ala Phe
                 -121-120         -115             -110

CTG ATC GGC ATA CAG GCG GAA CCA CAC TCA GAG AGC AAT GTC CCT GCA         99
Leu Ile Gly Ile Gln Ala Glu Pro His Ser Glu Ser Asn Val Pro Ala
            -105             -100                 -95

GGA CAC ACC ATC CCC CAA GTC CAC TGG ACT AAA CTT CAG CAT TCC CTT        147
Gly His Thr Ile Pro Gln Val His Trp Thr Lys Leu Gln His Ser Leu
            -90              -85                 -80

GAC ACT GCC CTT CGC AGA GCC CGC AGC GCC CCG GCA GCG GCG ATA GCT        195
Asp Thr Ala Leu Arg Arg Ala Arg Ser Ala Pro Ala Ala Ala Ile Ala
        -75              -70              -65

GCA CGC GTG GCG GGG CAG ACC CGC AAC ATT ACT GTG GAC CCC AGG CTG        243
Ala Arg Val Ala Gly Gln Thr Arg Asn Ile Thr Val Asp Pro Arg Leu
        -60              -55              -50

TTT AAA AAG CGG CGA CTC CGT TCA CCC CGT GTG CTG TTT AGC ACC CAG        291
Phe Lys Lys Arg Arg Leu Arg Ser Pro Arg Val Leu Phe Ser Thr Gln
-45             -40              -35              -30

CCT CCC CGT GAA GCT GCA GAC ACT CAG GAT CTG GAC TTC GAG GTC GGT        339
Pro Pro Arg Glu Ala Ala Asp Thr Gln Asp Leu Asp Phe Glu Val Gly
                -25              -20              -15

GGT GCT GCC CCC TTC AAC AGG ACT CAC AGG AGC AAG CGC TAC GCG GAG        387
Gly Ala Ala Pro Phe Asn Arg Thr His Arg Ser Lys Arg Tyr Ala Glu
            -10              -5                1

CAT AAG AGT CAC CGA GGG GAG TAC TCG GTA TGT GAC AGT GAG AGT CTG        435
His Lys Ser His Arg Gly Glu Tyr Ser Val Cys Asp Ser Glu Ser Leu
 5               10                  15

TGG GTG ACC GAC AAG TCA TCG GCC ATC GAC ATT CGG GGA CAC CAG GTC        483
Trp Val Thr Asp Lys Ser Ser Ala Ile Asp Ile Arg Gly His Gln Val
 20              25                  30                  35

ACG GTG CTG GGG GAG ATC AAA ACG GGC AAC TCT CCC GTC AAA CAA TAT        531
Thr Val Leu Gly Glu Ile Lys Thr Gly Asn Ser Pro Val Lys Gln Tyr
             40                  45                  50

TTT TAT GAA ACG CGA TGT AAG GAA GCC AGG CCG GTC AAA AAC GGT TGC        579
Phe Tyr Glu Thr Arg Cys Lys Glu Ala Arg Pro Val Lys Asn Gly Cys
             55                  60                  65

AGG GGT ATT GAT GAT AAA CAC TGG AAC TCT CAG TGC AAA ACA TCC CAA        627
Arg Gly Ile Asp Asp Lys His Trp Asn Ser Gln Cys Lys Thr Ser Gln
             70                  75                  80

ACC TAC GTC CGA GCA CTG ACT TCA GAG AAC AAT AAA CTC GTG GGC TGG        675
Thr Tyr Val Arg Ala Leu Thr Ser Glu Asn Asn Lys Leu Val Gly Trp
 85                  90                  95

CGG TGG ATA CGG ATA GAC ACG TCC TGT GTG TGT GCC TTG TCG AGA AAA        723
Arg Trp Ile Arg Ile Asp Thr Ser Cys Val Cys Ala Leu Ser Arg Lys
100                 105                 110                 115

ATC GGA AGA ACA TGAATTGGCA TCTCTCCCCA TATATAAATT ATTACTTTAA            775
Ile Gly Arg Thr
```

Ile Gly Arg Thr

ATTATATGAT ATGCATGTAG CATATAAATG TTTATATTGT TTTTATATAT TATAAGTTGA     835

CCTTTATTTA TTAAACTTCA GCAACCCTAC AGTATATAGG CTTTTTTCTC AATAAAATCA     895

GTGTGCTTGC CTTCCCTCAG GCAGATCT     923

(2) INFORMATION FOR SEQ ID NO:11:

(i) SEQUENCE CHARACTERISTICS:
        (A) LENGTH: 240 amino acids
        (B) TYPE: amino acid
        (D) TOPOLOGY: linear (ii) MOLECULE TYPE: protein (xi) SEQUENCE DESCRIPTION: SEQ ID NO:11:

```
Met Ser Met Leu Phe Tyr Thr Leu Ile Thr Ala Phe Leu Ile Gly Ile
-121 -120              -115             -110

Gln Ala Glu Pro His Ser Glu Ser Asn Val Pro Ala Gly His Thr Ile
-105             -100              -95              -90

Pro Gln Val His Trp Thr Lys Leu Gln His Ser Leu Asp Thr Ala Leu
             -85              -80              -75

Arg Arg Ala Arg Ser Ala Pro Ala Ala Ile Ala Ala Arg Val Ala
             -70              -65              -60

Gly Gln Thr Arg Asn Ile Thr Val Asp Pro Arg Leu Phe Lys Lys Arg
        -55              -50              -45

Arg Leu Arg Ser Pro Arg Val Leu Phe Ser Thr Gln Pro Pro Arg Glu
   -40              -35              -30

Ala Ala Asp Thr Gln Asp Leu Asp Phe Glu Val Gly Ala Ala Pro
-25              -20              -15              -10

Phe Asn Arg Thr His Arg Ser Lys Arg Tyr Ala Glu His Lys Ser His
             -5               1                5

Arg Gly Glu Tyr Ser Val Cys Asp Ser Glu Ser Leu Trp Val Thr Asp
         10              15              20

Lys Ser Ser Ala Ile Asp Ile Arg Gly His Gln Val Thr Val Leu Gly
     25              30              35

Glu Ile Lys Thr Gly Asn Ser Pro Val Lys Gln Tyr Phe Tyr Glu Thr
 40              45              50              55

Arg Cys Lys Glu Ala Arg Pro Val Lys Asn Gly Cys Arg Gly Ile Asp
             60              65              70

Asp Lys His Trp Asn Ser Gln Cys Lys Thr Ser Gln Thr Tyr Val Arg
             75              80              85

Ala Leu Thr Ser Glu Asn Asn Lys Leu Val Gly Trp Arg Trp Ile Arg
         90              95             100

Ile Asp Thr Ser Cys Val Cys Ala Leu Ser Arg Lys Ile Gly Arg Thr
    105             110             115
```

(2) INFORMATION FOR SEQ ID NO:12:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:12:

```
Tyr Ala Glu His Lys Ser His Arg Gly Glu Tyr Ser Val Cys Asp Ser
 1               5              10              15
```

```
        Glu Ser Leu Trp Val Thr Asp Lys Ser Ser Ala Ile Asp Ile Arg Gly
                     20                  25                  30

His Gln Val Thr Val Leu Gly Glu Ile Lys Thr Gly Asn Ser Pro Val
                     35                  40                  45

Lys Gln Tyr Phe Tyr Glu Thr Arg Cys Lys Glu Ala Arg Pro Val Lys
             50                  55                  60

Asn Gly Cys Arg Gly Ile Asp Asp Lys His Trp Asn Ser Gln Cys Lys
        65                  70                  75                  80

Thr Ser Gln Thr Tyr Val Arg Ala Leu Thr Ser Glu Asn Asn Lys Leu
                     85                  90                  95

Val Gly Trp Arg Trp Ile Arg Ile Asp Thr Ser Cys Val Cys Ala Leu
                     100                 105                 110

Ser Arg Lys Ile Gly Arg Thr
                     115
```